(12) United States Patent
Withers et al.

(10) Patent No.: US 10,023,601 B2
(45) Date of Patent: Jul. 17, 2018

(54) HYDROLYSIS RESISTANT SIALIC ACID DERIVATIVES AND METHODS FOR THEIR USE

(71) Applicant: The University of British Columbia, Vancouver (CA)

(72) Inventors: Stephen G. Withers, Vancouver (CA); Thomas J. Morley, New Haven, CT (US); Lars Baumann, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 8 days.

(21) Appl. No.: 15/119,622

(22) PCT Filed: Feb. 18, 2015

(86) PCT No.: PCT/CA2015/000096
§ 371 (c)(1),
(2) Date: Aug. 17, 2016

(87) PCT Pub. No.: WO2015/123756
PCT Pub. Date: Aug. 27, 2015

(65) Prior Publication Data
US 2017/0121361 A1 May 4, 2017

Related U.S. Application Data

(60) Provisional application No. 61/940,939, filed on Feb. 18, 2014.

(51) Int. Cl.
| | |
|---|---|
| *C07H 13/02* | (2006.01) |
| *C12P 21/00* | (2006.01) |
| *C07K 1/107* | (2006.01) |
| *C07H 5/02* | (2006.01) |
| *C08H 1/00* | (2006.01) |

(52) U.S. Cl.
CPC ............. *C07H 13/02* (2013.01); *C07H 5/02* (2013.01); *C07K 1/1077* (2013.01); *C08H 1/00* (2013.01); *C12P 21/005* (2013.01)

(58) Field of Classification Search
None
See application file for complete search history.

(56) References Cited

U.S. PATENT DOCUMENTS 5,627,290 A  5/1997  Iida et al.

FOREIGN PATENT DOCUMENTS

| CA | 2491594 A1 | 1/2004 |
| WO | WO 91/09975 | 7/1991 |

OTHER PUBLICATIONS

Hartlieb, S. et al., "Chemoenzymatic synthesis of CMP-N-acetyl7-fluoro-7-deoxy-neuraminic acid." *Carbohydrate Research*, 2008, 343: 2075-2082.

Thomson, R., von Itzstein, M., "Synthesis of 4-substituted-2-acetamido-2,4-dideoxy-mannopyranoses using 1,6-anhydro sugar chemistry." *Carbohydrate Research*, 1995, 274: 29-44.

Burkart, M. D. et al., "An efficient synthesis of CMP-3-fluoroneuraminic acid." *Chem. Commun.*, 1999, 1525-1526.

Cao, H. et al., "Sialidase substrate specificity studies using chemoencymatically synthesized sialosides containing C5-modified sialic acids." *Organic & Biomolecular Chemistry*, Oct. 2009, 7: 5137-5145, DOI: 10.1039/b916305k.

(Continued)

*Primary Examiner* — Eric Olson
(74) *Attorney, Agent, or Firm* — Saliwanchik, Lloyd & Eisenschenk

(57) ABSTRACT

This invention provides compound having a structure of Formulas: Furthermore, methods and uses of such compounds for covalently bonding to a sugar acceptor, to form modified protein therapeutics having reduced enzymatic hydrolysis, improved biological stability or an improved pharmacokinetic property.

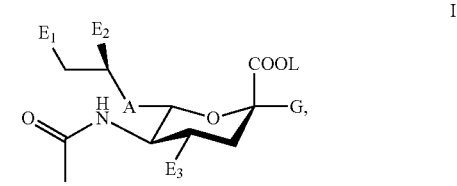

I

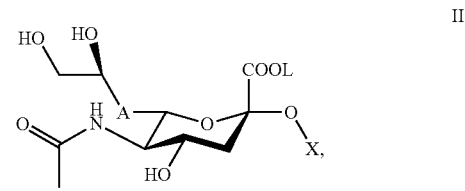

II

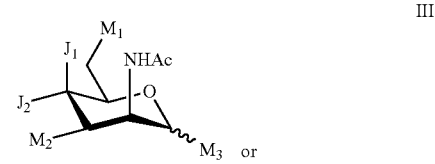

III

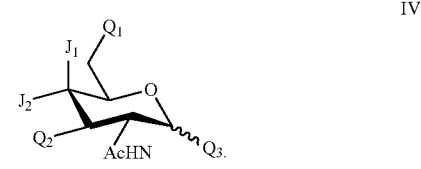

IV

6 Claims, 6 Drawing Sheets

(56) References Cited

OTHER PUBLICATIONS

Chiu, C. P. C. et al, "Structural analysis of the sialyltransferase CstII from Campylobacter jejuni in complex with a substrate analog." *Nature Structural & Molecular Biology*, Feb. 2004, 11(2): 163-170, DOI: 10.1038/nsmb720.

Chiu, C.P.C. et al., "Structural Analysis of the R-2,3-Sialyltransferase Cst-I from Campylobacter jejuni in Apo and Substrate-Analogue Bound Forms†." *Biochemistry*, 2007, 7196-7204, DOI: 10.1021/bi602543d.

Dabrowski, U. et al., "'H-NMR studies at N-acetyl-D-Neuraminic Acid Ketosides for the Determination of the Anomeric Configuration II." *Tetrahedron Letters*, 1979, 48: 4637-4640.

Gosselin, S. et al., "A Continuous Spectrophotometric Assay for Glycosyltransferases." *Analytical Biochemistry*, 1994: 220: 92-97.

Harrison, J. A., "Hydrolase and Sialyltransferase Activities of Trypanosoma cruzi trans-Sialidase Towards NeuAc-α-2,3-Gal—O—PNP." *Bioorganic & Medicinal Chemistry Letters*, 2001, 11: 141-144.

Hemeon, I., Bennet, A. J., "Sialic Acid and Structural Analogues: Stereoselective Syntheses." *Synthesis*, 2007, 13: 1899-1926, DOI: 10.1055/s-2007-983723.

Honda, T. et al., "Synthesis and Anti-Influenza Virus Activity of 4-Guanidino-7-substituted Neu5Ac2en Derivatives." *Bioorganic & Medicinal Chemistry Letters*, 2002, 12: 1921-1924.

Horenstein, B. A., Bruner, M., "Acid-Catalyzed Solvolysis of CMP-N-Acetyl Neuraminate: Evidence for a Sialyl Cation with a Finite Lifetime." *J. Am. Chem. Soc.*, 1996, 118: 10371-10379.

Hu, S. et al., "Coupled bioconversion for preparation of N-acetyl-Dneuraminic acid using immobilized N-acetyl-D-glucosamine-2-epimerase and N-acetyl-D-neuraminic acid lyase." *Appl. Microbiol. Biotechnol.*, 2010, 85: 1383-1391, DOI: 10.1007/s00253-009-2163-9.

Indurugalla, D. et al., "Natural sialoside analogues for the determination of enzymatic rate constants." *Org. Biomol. Chem.*, 2006, 4: 4453-4459, DOI: 10.1039/b613909d.

Kao, Y. et al., "Stereoselectivity of the Chinese hamster ovary cell sialidase: sialoside hydrolysis with overall retention of configuration." *Glycobiology*, 1997, 7(4): 559-563.

Karwaski, M. et al., "High-level expression of recombinant *Neisseria* CMP-sialic acid synthetase in *Escherichia coli*." *Protein Expression and Purification*, 2002, 25: 237-240.

Lemieux, R. U., Stevens, J. D., "Substitutional and Configuration Effects on Chemical Shift in Pyranoid Carbohydrate Derivatives." *Canadian Journal of Chemistry*, 1965, 43: 2059-2070.

Mizanur, R. M., Pohl, N. L., "Bacterial CMP-sialic acid synthetases: production, properties, and applications." *Appl. Microbiol. Biotechnol.*, 2008, 80: 757-765, DOI: 10.1007/s00253-008-1643-7.

Morley, T. J., Withers, S. G., "Chemoenzymatic Synthesis and Enzymatic Analysis of 8-Modified Cytidine Monophosphate-Sialic Acid and Sialyl Lactose Derivatives." *J. Am. Chem. Soc.*, 2010, 132: 9430-9437, DOI: 10.1021/ja102644a.

Nahálka, J., Pätoprstý, V., "Enzymatic synthesis of sialylation substrates powered by a novel polyphosphate kinase (PPK3)." *Org. Biomol. Chem.*, 2009, 7: 1778-1780, DOI: 10.1039/b822549b.

Namchuk, M. N. et al., "The Role of Sugar Substituents in Glycoside Hydrolysis." *J. Am. Chem. Soc.*, 2000, 122: 1270-1277, DOI: 10.1021/ja992044h.

Newstead, S. L. et al., "The Structure of Clostridium perfringens NanI Sialidase and Its Catalytic Intermediates." *Journal of Biological Chemistry*, Apr. 2008, 283(14): 9080-9089.

Ni, L. et al., "Crystal Structures of Pasteurella multocida Sialyltransferase Complexes with Acceptor and Donor Analogues Reveal Substrate Binding Sites and Catalytic Mechanism." *American Chemical Society*, 2007, 46: 6288-6298, DOI: 10.1021/bi700346w.

Ress, D. K., Linhardt, R. J., "Sialic Acid Donors: Chemical Synthesis and Glycosylation." *Current Organic Synthesis*, 2004, 1:31-46.

Sharma, M. et al., "Fluorinated carbohydrates as potential plasma membrane modifiers. Synthesis of 3-deoxy-3-fluoro derivatives of 2-acetamido-2-deoxy-D-hexopyranoses." *Carbohydrate Research*, 1993, 240: 85-93.

Watts, A. G., et al., "Structural and Kinetic Analysis of Two Covalent Sialosyl-Enzyme Intermediates on Trypanosoma rangeli Sialidase." *Journal of Biological Chemistry*, 2006, 281(7): 4149-4156, DOI: 10.1074/jbc.M510677200.

Watts, A. G., Withers, S. G., "The synthesis of some mechanistic probes for sialic acid processing enzymes and the labeling of a sialidase from Trypanosoma rangeli." *Can. J. Chem.*, 2004, 82: 1581-1588, DOI: 10.1139/V04-125.

Withers, S. G., et al., "The Synthesis and Hydrolysis of a Series of Deoxyfluoro-D-Glucopyranosyl Phosphates." *Carbohydrate Research*, 1986, 154: 127-144.

Zhang, R. et al., "Synthesis and Testing of 2-Deoxy-2,2-Dihaloglycosides as Mechanism-Based Inhibitors of α-Glycosidases." *J. Org. Chem.*, 2008, 73: 3070-3077, DOI: 10.1021/jo702565q.

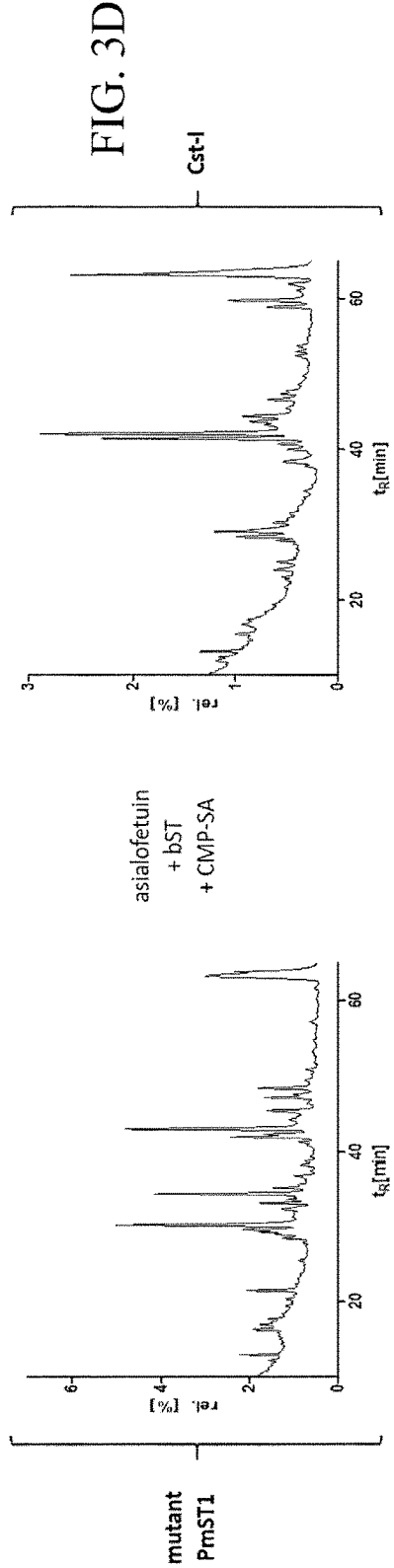
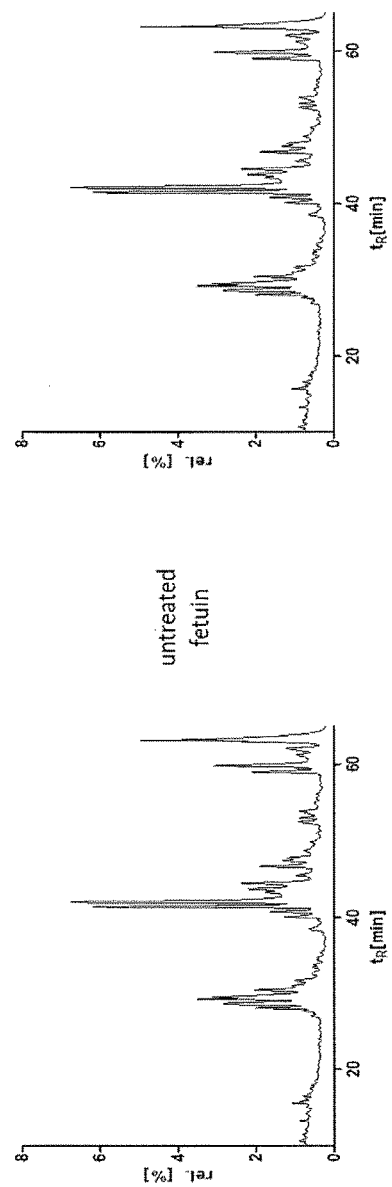
FIG. 3D
FIG. 3E

1. CMP-SA + dextran 40 kDa
2. CMP-SA
3. CMP-7FSA + dextran 40kDa
4. CMP-7FSA
5. w/o

HYDROLYSIS RESISTANT SIALIC ACID DERIVATIVES AND METHODS FOR THEIR USE

CROSS REFERENCE TO A RELATED APPLICATION

This application is a National Stage Application of International Patent Application No. PCT/CA2015/000096, filed Feb. 18, 2015; which claims the benefit of U.S. Provisional Patent Application Ser. No. 61/940,939, filed on Feb. 18, 2014 both of which are incorporated herein by reference in their entirety.

TECHNICAL FIELD

This invention relates to modified sugars, and uses and methods for reducing rates of hydrolysis of glycoproteins, including glycoprotein therapeutics. In particular the invention relates to improved glycoprotein and glycopeptide pharmacokinetic profile and/or circulatory half-life.

BACKGROUND

Protein therapeutics have gained significance in the past 25 years, with over 130 protein and peptide based therapeutic agents currently approved by the FDA[1-5] for treatment of a range of disease states including diabetes[6], anaemia[7] and Hepatitis C[8]. Protein therapeutics may have advantages over small molecule therapeutics in that they can be highly specific and off-target effects may be minimised. Furthermore, protein based therapeutic agents may also be used in replacement therapies to restore normal function[3]. However, protein and peptide based therapeutics may have risks associated with detrimental immune responses to the recombinant proteins[9], and are generally more complex and expensive to produce[10].

Almost all extracellular mammalian proteins are glycosylated[11], and the functions and physical properties of these proteins are highly dependent on the structure and level of glycosylation[12]. Of the carbohydrates present in these glycans the terminal sugar is most often sialic acid[13]. As the point of first contact for protein-receptor interactions, sialic acid plays an important role in the physical and biological properties of the glycoprotein. The presence of sialic acid on glycoproteins is intrinsically linked to plasma half life[14]. This may be exemplified by a synthetic, hyperglycosylated erythropoiesis-stimulating agent that showed a significantly increased half-life in serum due to suppression of the clearance mechanism, mediated by the liver[15, 16], thereby effectively boosting the efficacy of the drug[7-17]. The receptors in the liver that are responsible for binding to and clearing glycoproteins will often recognise a terminal galactose residue. Sialic acid is commonly found linked to galactose and so its presence on the glycan terminus effectively acts as a mask for the galactose, blocking the binding of the glycoprotein to the asialo-receptors in the liver and reducing the clearance rate.

The action of any mammalian sialidases (sialic acid hydrolysing enzymes)[18] on a glycoprotein is to remove the terminal sialic acid to expose the terminal galactose. Once this residue is exposed the protein or peptide is effectively targeted for clearance from the circulation. Thus proteins that possess glycans bearing sialidase-resistant sialosides have the potential for increased serum half-lives. This concept may be used to boost the efficacy of any synthetic, therapeutic glycoprotein or glycopeptide, provided a suitable, stable, and non-immunogenic sialic acid derivative can be found that can be readily transferred to any glycoprotein. Since spontaneous (non-enzymatic) sialoside cleavage may also be important, any substitutions on the sialic acid that minimize that process could also be of value.

A number of approaches have been described to produce sialidase-resistant sialosides, including the use of sulfur-linked sialosides[19]. Replacement of the normal oxygen linkage with a sulfur rendered these S-linked sialosides far more resistant to chemical or enzymatic hydrolysis compared with their O-linked homologues. Such an approach has proven useful in providing stable sialosides to probe the binding affinities and specificities of sialic acid binding proteins[20,21], and also in antibody generation towards vaccine synthesis[22,23]. Furthermore, stable sialosides have proven to be highly effective inhibitors of the sialidases of *T. rangeli*[24], *T. cruzi*[25], rotavirus[26] and influenza virus[27].

It has also been found that introduction of fluorine to the 3 position of sialic acid derivatives greatly increases the stability of the glycosidic bond. This is likely due to the close proximity of the highly electronegative fluorine atom to the anomeric carbon thereby inductively destabilizing any oxocarbenium ion-like transition state and greatly increasing the activation energy for bond cleavage. This concept has been used to great effect in the study of sialidases, by allowing trapping of a 3-fluoro sialosyl-enzyme covalent intermediate[28-30], and also of sialyltransferases, by providing a stable sialyl donor sugar (CMP 3-fluoro sialic acid 2)[31-34].

SUMMARY

This invention is based in part on the discovery that compounds described herein when incorporated into a glycoprotein or glycolipid may assist in reducing enzymatic hydrolysis, improving the biological stability or improving a pharmacokinetic property of associated glycoproteins or glycolipids. Specifically, compounds identified herein, show the ability to reduce enzymatic hydrolysis of an associated glycoprotein or glycolipid following incorporation therein. Furthermore, this invention is also based in part on the fortuitous discovery that the transferase used to incorporate the sugar is not similarly slowed by the modifications incorporated into the sialic acids described herein. Accordingly, the modified sialic acids may be efficiently incorporated into a glycoconjugate (for example a glycoprotein or a glycolipid).

In accordance with a first embodiment there is provided a compound of Formula I or a pharmaceutically acceptable salt thereof:

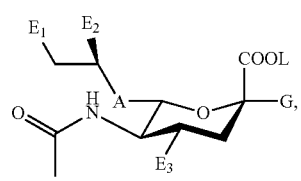

I wherein A may be

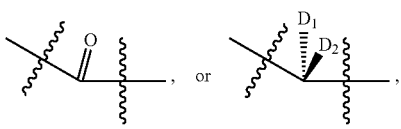

$D_1$ and $D_2$ may be independently selected from H, F, Cl, and Br; $E_1$, $E_2$ and $E_3$ may be independently selected from OH and an ester; L may be H, Me, Et, Pr, Bu, pentyl, hexyl, heptyl, octyl, nonyl, or decyl; G may be OH, CMP, AMP, UMP, GMP, IMP, or TMP, a substituted phenol, wherein the substituted phenol provides a leaving group of comparable reactivity; provided that both $D_1$ and $D_2$ are not both H; and provided that when L is H and G is OH, A may be selected from

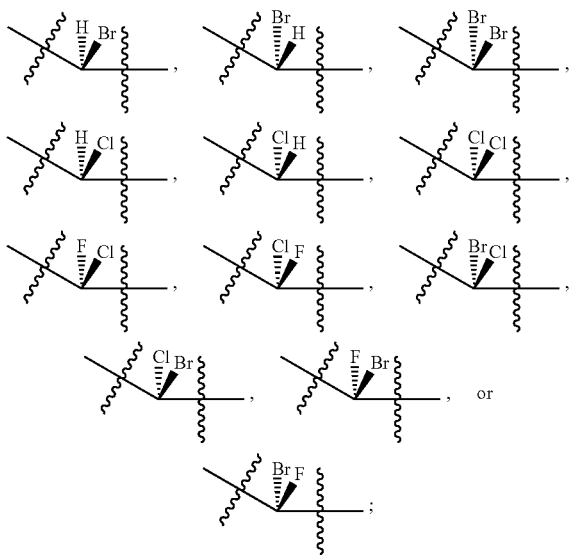

and provided that when L is Me and G is OH, A may be selected from

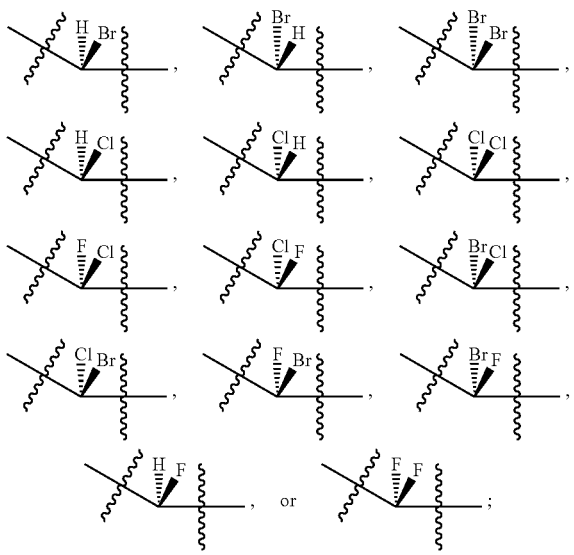

and provided that when L is H and G is CMP, A may be selected from

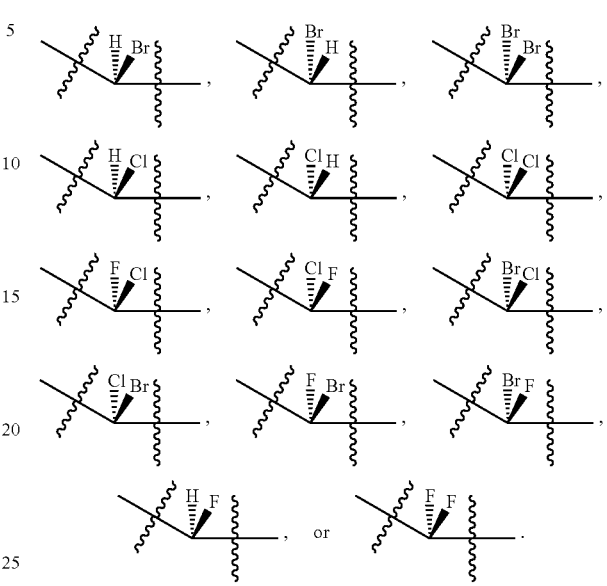

In accordance with a further embodiment there is provided a compound of Formula I or a pharmaceutically acceptable salt thereof:

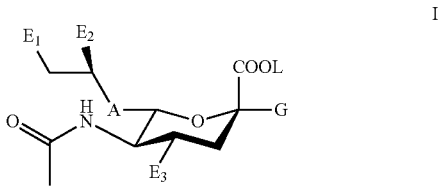

I wherein A may be

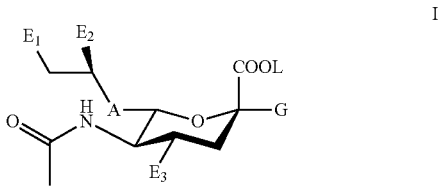

$D_1$ and $D_2$ may be independently selected from H, F, Cl, and Br; $E_1$, $E_2$ and $E_3$ may be independently selected from OH and an ester; L may be H, Me, Et, Pr, Bu, pentyl, hexyl, heptyl, octyl, nonyl, or decyl; G may be OH, CMP, a substituted phenol, wherein the substituted phenol provides a leaving group of comparable reactivity, or another leaving group of comparable reactivity; provided that both $D_1$ and $D_2$ are not both H; and provided that when L is H and G is OH, A may be selected from

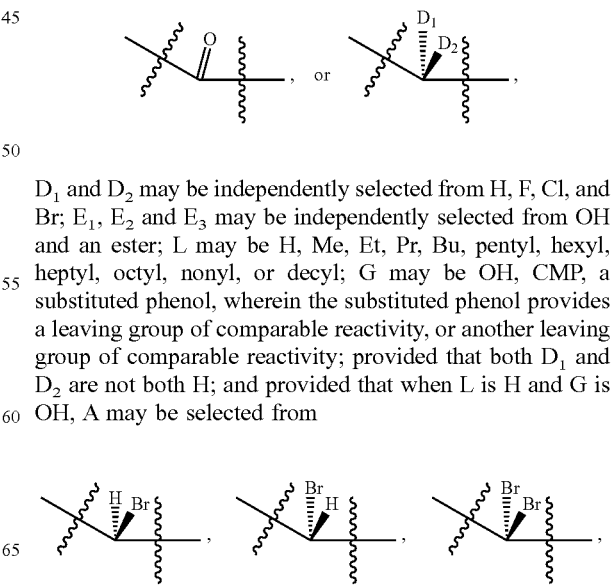

-continued

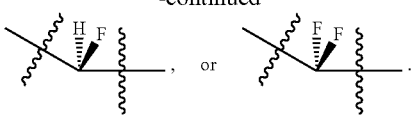

In accordance with a further embodiment there is provided a compound of Formula I, wherein the compound has the structure

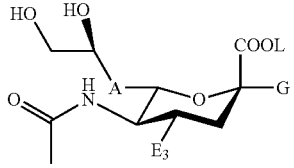

or a pharmaceutically acceptable salt thereof; wherein A may be and provided that when L is Me and G is OH, A may be selected from

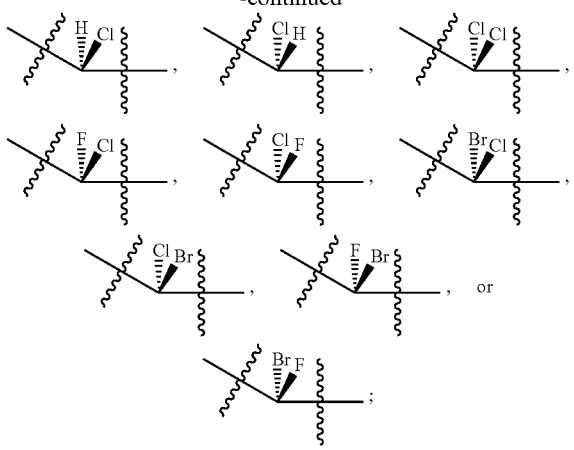

wherein $D_1$ and $D_2$ may be independently selected from H, F, Cl, and Br or $D_1$ and $D_2$ may be independently selected from H, F and Cl or $D_1$ and $D_2$ may be independently selected from H, F and Br or $D_1$ and $D_2$ may be independently selected from H and F; wherein L may be H or an alkyl chain or L may be H or a branched alkyl chain or L may be H or a linear alkyl chain or L may be H, Me, Et, Pr, Bu, pentyl, hexyl, heptyl, octyl, nonyl or decyl or L may be H; G may be a leaving group or G may be H or G may be OH, CMP, AMP, UMP, GMP, IMP, TMP, or a substituted phenol, wherein the substituted phenol provides a leaving group of comparable reactivity or G may be OH, CMP or a substituted phenol or G may be OH, CMP or a substituted phenol, wherein the substituted phenol provides a leaving group of comparable reactivity or G may be OH, CMP, or O-nitrophenyl. G may be CMP, or O-nitrophenyl or G may be OH or CMP. G may be OH or O-nitrophenyl or G may be OH or CMP. Provided that both $D_1$ and $D_2$ should not both be H, provided that when L is H and G is OH, A may be selected from and provided that when L is H and G is CMP, A may be selected from

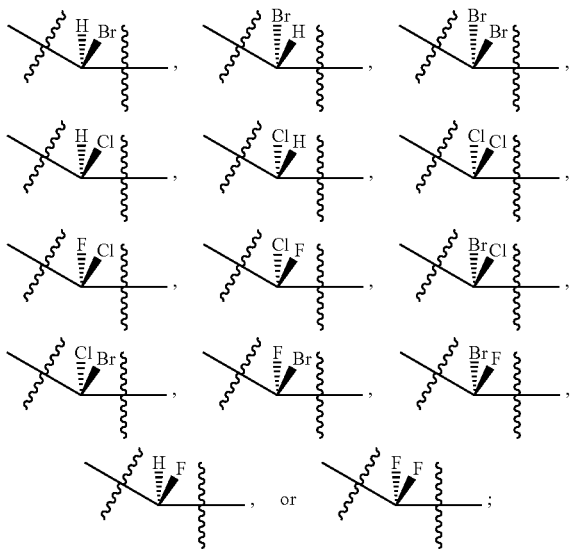

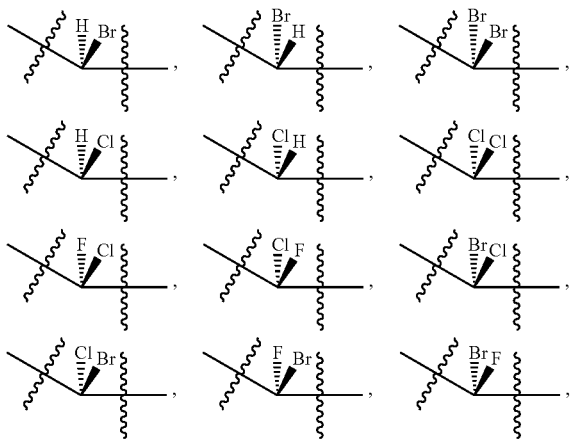

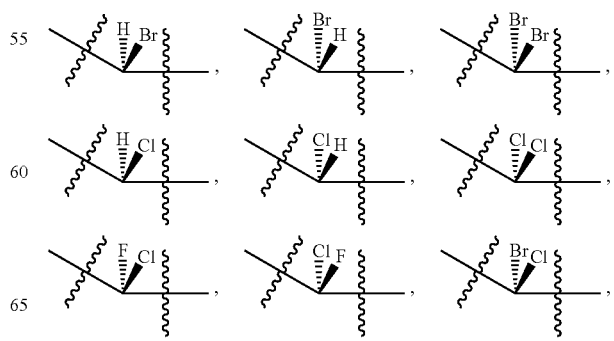

-continued

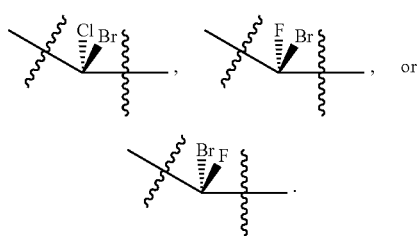

Or provided that when L is Me and G is OH, A may be selected from

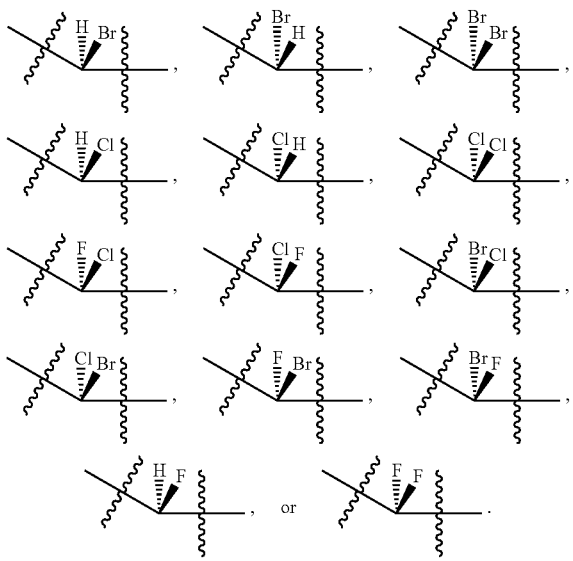

Or provided that when L is H and G is CMP, A may be selected from

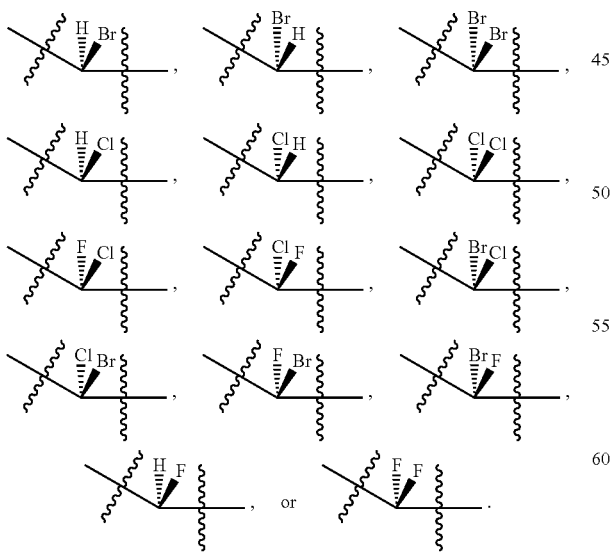

Or provided that when L is H and G is OH, A may be selected from

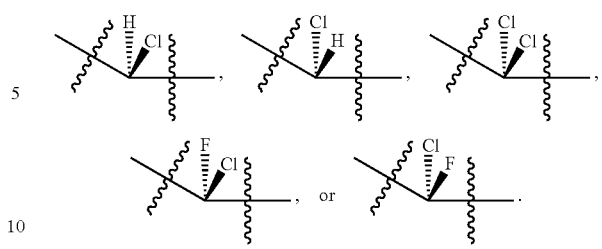

Or provided that when L is Me and G is OH, A may be selected from

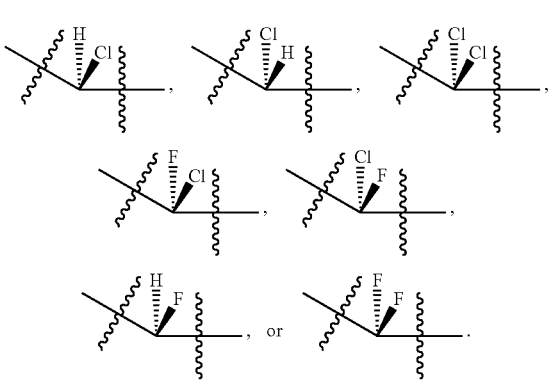

Or provided that when L is H and G is CMP, A may be selected from

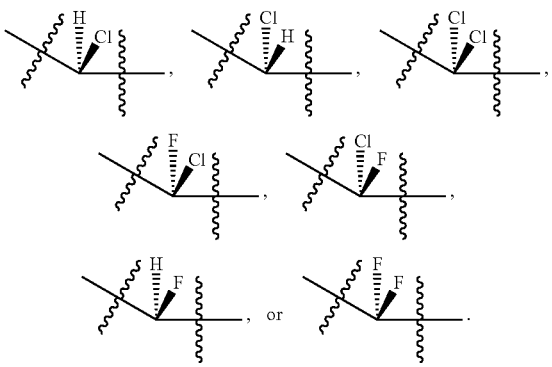

In accordance with a further embodiment there is provided a compound of Formula II or a pharmaceutically acceptable salt thereof:

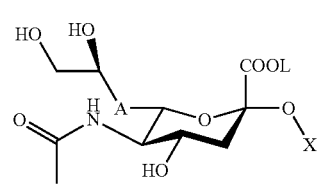

II wherein A may be

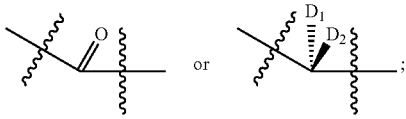

$D_1$ and $D_2$ may be independently selected from H, F, Cl, and Br; L may be H or $CH_3$; X may be a sialic acid, a modified sialic acid, a glucose, a galactose, a mannose, a fucose, an acetylgalactosamine, an acetylglucosamine, an acetylgalactosamine thiazoline, an acetylglucosamine thiazoline, an acetylneuraminic acid, or a xylose; provided that both $D_1$ and $D_2$ are not both H. A may be

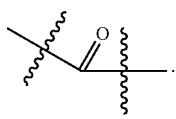

A may be

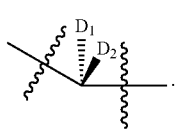

$D_1$ and $D_2$ may be independently selected from H, F or Cl. $D_1$ and $D_2$ may be independently selected from H or F, provided that both $D_1$ and $D_2$ are not both H. L may be H. L may be $CH_3$.

In accordance with a further embodiment there is provided a method of protein production, the method including: (a) transforming a cell with a nucleic acid encoding for a protein of interest; (b) culturing the cell in cell media that comprises a compound of Formula III or IV:

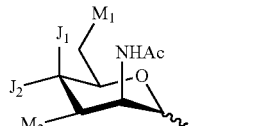

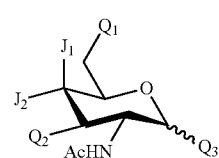

wherein $M_1$, $M_2$ and $M_3$ may be independently selected from OH or an ester; $Q_1$, $Q_2$ and $Q_3$ may be independently selected from OH or an ester; $J_1$ and $J_2$ may be independently selected from H, F, Cl, and Br; provided that both $J_1$ and $J_2$ may not both be H or F; and provided that when $J_2$ is H, $J_1$ may be Cl or Br; and provided that when $J_2$ is F, $J_1$ may be Cl or Br.

In accordance with a further embodiment there is provided a use of a compound of Formula I or a pharmaceutically acceptable salt thereof:

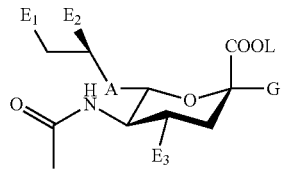

wherein A may be

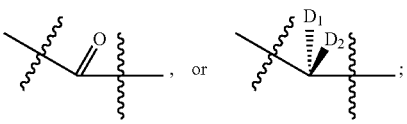

$D_1$ and $D_2$ may be independently selected from H, F, Cl, Br; $E_1$, $E_2$ and $E_3$ may be independently selected from OH or an ester; L may be H, Me, Et, Pr, Bu, pentyl, hexyl, heptyl, octyl, nonyl, or decyl; and G may be OH, CMP, AMP, UMP, GMP, IMP, or TMP, a substituted phenol; provided that both $D_1$ and $D_2$ are not both H; to modify a protein or a lipid.

In accordance with a further embodiment there is provided a use of a compound of Formula II:

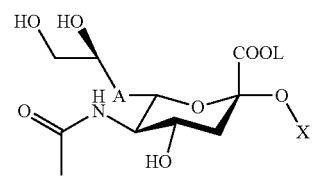

wherein A may be

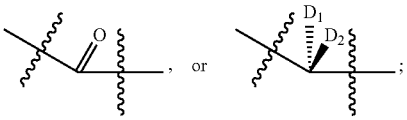

$D_1$ and $D_2$ may be independently selected from H, F, Cl, Br; L may be H or $CH_3$; X may be a sialic acid, a modified sialic acid, a D-Glucose, a D-Galactose, a D-Mannose, an L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose; provided that both $D_1$ and $D_2$ may not both be H; to modify a protein or a lipid.

In accordance with a further embodiment there is provided a use of a compound of Formula III or IV:

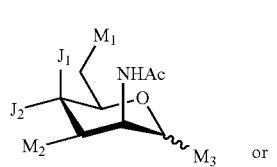

-continued

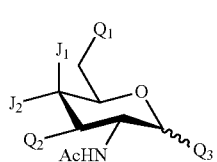
IV wherein $M_1$, $M_2$ and $M_3$ may be independently selected from OH or an ester; $Q_1$, $Q_2$ and $Q_3$ may be independently selected from OH or an ester; $J_1$ and $J_2$ may be independently selected from H, F, Cl, and Br; provided that both $J_1$ and $J_2$ may not both be H or F; and provided that when $J_2$ is H, $J_1$ may not be Cl or Br; and provided that when $J_2$ is F, $J_1$ may not be Cl or Br; to modify a protein or a lipid. In accordance with a further embodiment there is provided a compound of Formula III or IV:

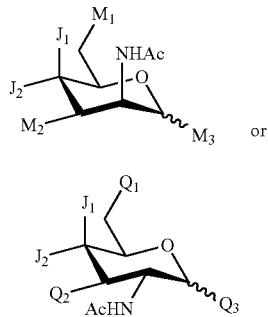

wherein $M_1$, $M_2$ and $M_3$ may be independently selected from OH or an ester; $Q_1$, $Q_2$ and $Q_3$ may be independently selected from OH or an ester; $J_1$ and $J_2$ may be independently selected from H, F, Cl, and Br; provided that both $J_1$ and $J_2$ may not be both H or F; and provided that when $J_2$ is H, $J_1$ may be Cl or Br; and provided that when $J_2$ is F, $J_1$ may be Cl or Br.

In accordance with a further embodiment there is provided a compound of Formula III or IV:

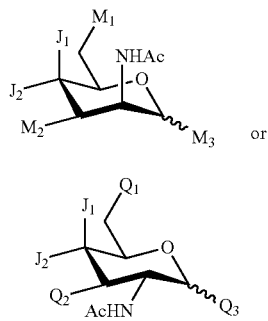

wherein $M_1$, $M_2$ and $M_3$ may be independently selected from OH or an ester; $Q_1$, $Q_2$ and $Q_3$ may be independently selected from OH or an ester; $J_1$ and $J_2$ may be independently selected from H, F and Cl; provided that both $J_1$ and $J_2$ may not be both H or F; and provided that when $J_2$ is H, $J_1$ may be Cl; and provided that when $J_2$ is F, $J_1$ may be Cl.

In accordance with a further embodiment there is provided a method of protein production, the method including:

(a) transforming a sialic acid biosynthesis negative cell with a nucleic acid encoding for a protein of interest; and (b) culturing the cell in cell media that comprises a compound of Formula I or a pharmaceutically acceptable salt thereof:

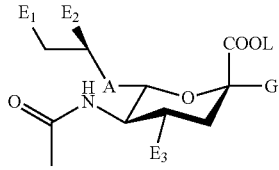
I wherein A may be

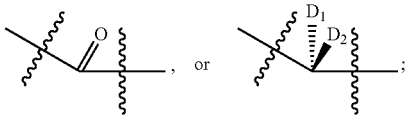

$D_1$ and $D_2$ may be independently selected from H, F, Cl, Br; $E_1$, $E_2$ and $E_3$ may be independently selected from OH or an ester; L may be H, Me, Et, Pr, Bu, pentyl, hexyl, heptyl, octyl, nonyl, or decyl; and G is OH, CMP, AMP, UMP, GMP, IMP, or TMP, a substituted phenol; provided that both $D_1$ and $D_2$ may not both be H.

In accordance with a further embodiment there is provided a method of forming a covalent conjugate between a sugar acceptor and a compound of Formula I or a pharmaceutically acceptable salt thereof, the method comprising contacting the sugar acceptor and compound of Formula I or a pharmaceutically acceptable salt thereof, the contacting step taking place under conditions suitable for reacting and covalently bonding the compound of Formula I to the sugar acceptor.

In accordance with a further embodiment there is provided a compound of Formula I, II, III or IV for modifying a protein or a glycolipid.

In accordance with a further embodiment there is provided a pharmaceutical composition, including a compound of Formula I or II or a pharmaceutically acceptable salt thereof, and a therapeutic protein, wherein the compound of Formula I or II and the therapeutic protein are covalently bound.

In accordance with a further embodiment there is provided a pharmaceutical composition, including a compound of Formula I or II or a pharmaceutically acceptable salt thereof, covalently bound to a therapeutic protein and a pharmaceutically acceptable carrier.

In accordance with a further embodiment there is provided a commercial package including: (a) a compound Formula I, II III or IV; and (b) an enzyme capable of transferring the compound of Formula I, II, III or IV, to a sugar acceptor on a protein or a glycolipid.

In accordance with a further embodiment there is provided a commercial package including: (a) a compound Formula I, II III or IV; (b) an enzyme capable of transferring the compound of Formula I, II, III or IV, to a sugar acceptor on a protein or a glycolipid; and (c) instructions for the use thereof for modifying the protein or a glycolipid.

The substituted phenol may, for example, be O-nitrophenyl or a leaving group of comparable reactivity. Alternatively, the substituted phenol may be substituted such that the substituted phenol provides a leaving group of comparable reactivity.

A may be

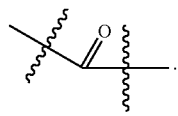 [SMILES: *C(*)=O]

A may be

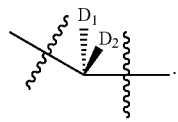

$D_1$ and $D_2$ may be independently selected from H, F, Cl, and Br. $D_1$ and $D_2$ may be independently selected from H, F and Cl. $D_1$ and $D_2$ may be independently selected from H, F and Br. $D_1$ and $D_2$ may be independently selected from H and F. Both $D_1$ and $D_2$ should not both be H. When L is H and G is OH, A may be selected from

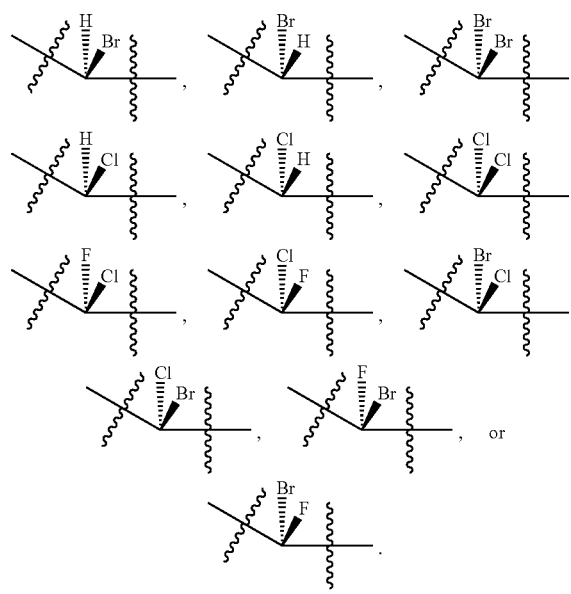

When L is Me and G is OH, A may be selected from

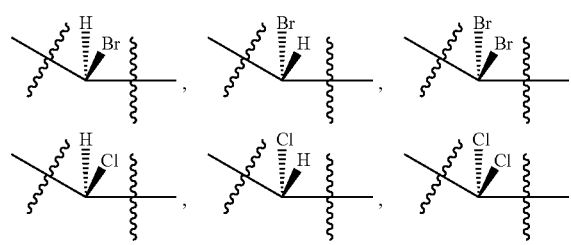

-continued

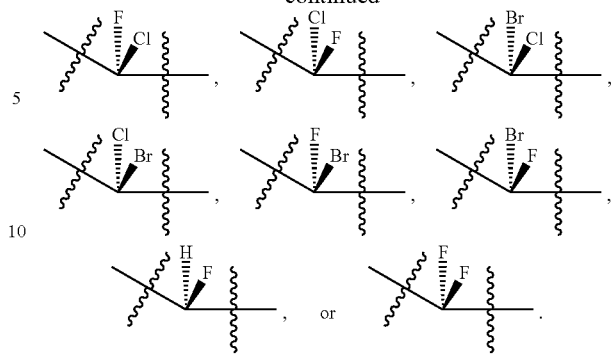

When L is H and G is CMP, A may be selected from

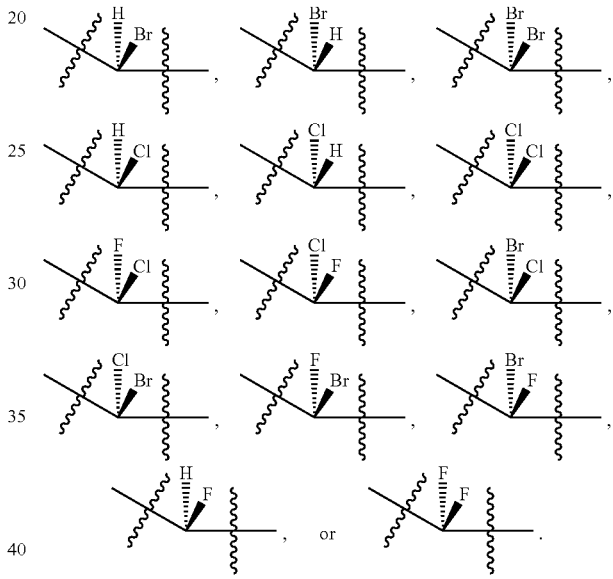

When L is H and G is OH, A may be selected from

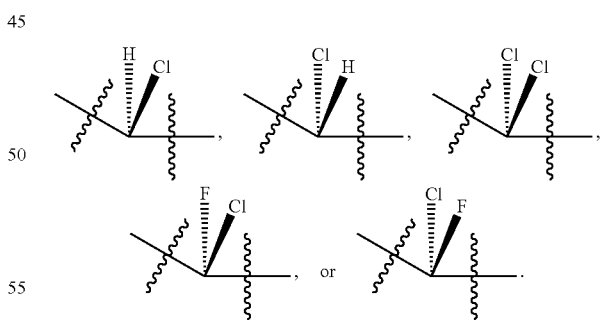

When L is Me and G is OH, A may be selected from

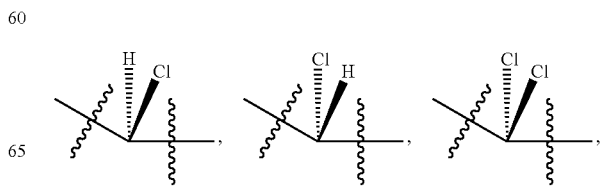

-continued

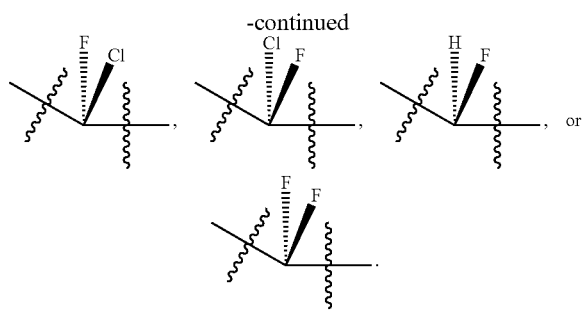

When L is H and G is CMP, A may be selected from

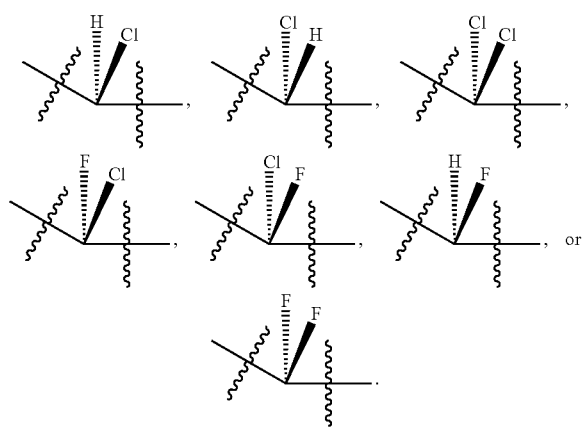

$E_1$, $E_2$ and $E_3$ may be independently selected from OH and an ester, wherein the ester may be selected from a linear or branched acetate, a linear branched propionate, a linear or branched butyrate, a linear branched pentanoate, a linear or branched hexanoate, a linear or branched heptanoate, a linear or branched octanoate, a linear or branched nonanoate, or a linear or branched decanoate. $E_1$, $E_2$ and $E_3$ may each be OH. $E_1$, $E_2$ and $E_3$ may each independently be OH, an acetate, a propionate, a butyrate, a pentanoate, a hexanoate, a heptanoate, a octanoate, a nonanoate, or a decanoate. $E_1$, $E_2$ and $E_3$ may each independently be OH, an acetate, a propionate, a butyrate, a pentanoate, a hexanoate, a heptanoate, a octanoate, or a nonanoate. $E_1$, $E_2$ and $E_3$ may each independently be OH, an acetate, a propionate, a butyrate, a pentanoate, a hexanoate, a heptanoate, or a octanoate. $E_1$, $E_2$ and $E_3$ may each independently be OH, an acetate, a propionate, a butyrate, a pentanoate, a hexanoate, or a heptanoate. $E_1$, $E_2$ and $E_3$ may each independently be OH, an acetate, a propionate, a butyrate, a pentanoate, or a hexanoate. $E_1$, $E_2$ and $E_3$ may each independently be OH, an acetate, a propionate, a butyrate, or a pentanoate. $E_1$, $E_2$ and $E_3$ may each independently be OH, an acetate, a propionate, or a butyrate. $E_1$, $E_2$ and $E_3$ may each independently be OH, an acetate, or a propionate.

L may be H or an alkyl chain. L may be H or a branched alkyl chain. L may be H or a linear alkyl chain. L may be H, Me, Et, Pr, Bu, pentyl, hexyl, heptyl, octyl, nonyl or decyl. L may be H, Me, Et, Pr, Bu, pentyl, hexyl, heptyl, octyl or nonyl. L may be H, Me, Et, Pr, Bu, pentyl, hexyl, heptyl or octyl. L may be H, Me, Et, Pr, Bu, pentyl, hexyl or heptyl. L may be H, Me, Et, Pr, Bu, pentyl or hexyl. L may be H, Me, Et, Pr, Bu or pentyl. L may be H, Me, Et, Pr or Bu. L may be H, Me, Et or Pr. L may be H, Me or Et. L may be H or Me. L may be H.

G may be a leaving group. G may be H. G may be OH, CMP, AMP, UMP, GMP, IMP, TMP, or a substituted phenol, wherein the substituted phenol provides a leaving group of comparable reactivity. G may be OH, CMP or a substituted phenol. G may be OH, CMP or a substituted phenol, wherein the substituted phenol provides a leaving group of comparable reactivity. G may be OH, CMP, or O-nitrophenyl. G may be CMP, or O-nitrophenyl. G may be OH or CMP. G may be OH, or O-nitrophenyl. G may be OH, or CMP. It will be appreciated by a person of skill in the art that having a nucleoside monophosphate at the G position may result in the compound connecting to the nucleoside monophosphate via an oxygen, since for example, CMP has 4 oxygens on its phosphate and the derivative would have four oxygens at that position.

The ester may be independently selected from one or more of the following: a linear or branched acetate, a linear or branched propionate, a linear or branched butyrate, a linear or branched pentanoate, a linear or branched hexanoate, a linear or branched heptanoate, a linear or branched octanoate, a linear or branched nonanoate, or a linear or branched decanoate. The ester may be a linear or branched acetate, a linear or branched propionate, a linear or branched butyrate, a linear or branched pentanoate, a linear or branched hexanoate, a linear or branched heptanoate, a linear or branched octanoate, or a linear or branched nonanoate. The ester may be a linear or branched acetate, a linear or branched propionate, a linear or branched butyrate, a linear or branched pentanoate, a linear or branched hexanoate, a linear or branched heptanoate, or a linear or branched octanoate. The ester may be a linear or branched acetate, a linear or branched propionate, a linear or branched butyrate, a linear or branched pentanoate, a linear or branched hexanoate, or a linear or branched heptanoate.

The ester may be a linear or branched acetate, a linear or branched propionate, a linear or branched butyrate, a linear or branched pentanoate, or a linear or branched hexanoate. The ester may be a linear or branched acetate, a linear or branched propionate, a linear or branched butyrate, or a linear or branched pentanoate. The ester may be linear. The ester may be branched.

The compound may further include one or more saccharide groups attached from the 2 carbon position. The one or more saccharide group may be selected from one or more of the following: a sialic acid, a modified sialic acid, a glucose, a galactose, a mannose, a fucose, an acetylgalactosamine, an acetylglucosamine, an acetylgalactosamine, thiazoline an acetylglucosamine thiazoline, an acetylneuraminic acid, or a xylose.

The one or more saccharide groups may be selected from one or more of the following: a sialic acid, a modified sialic acid, a D-Glucose, a β-D-Galactose, a β-D-Mannose, an α-L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose. The one or more saccharide groups may be selected from one or more of the following: a sialic acid, a modified sialic acid, a β-D-Glucose, a β-D-Galactose, a β-D-Mannose, an α-L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose The compound may be further covalently bound to a protein or a glycolipid. The glycoprotein may be mucin-linked. The glycoprotein may be asparagine-linked.

The compound may be further covalently bound to a glycoprotein. The glycoprotein may be mucin-linked. The glycoprotein may be asparagine-linked. The compound may further include one or more saccharide groups attached from the 2 carbon position. The one or more saccharide group may be selected from one or more of the following: a sialic acid, a modified sialic acid, a Glucose, a Galactose, a Mannose, an Fucose, a Acetylgalactosamine, a Acetylglucosamine, a Acetylgalactosamine thiazoline, a Acetylglucosamine thiazoline, a Acetylneuraminic acid, or a Xylose. The one or more saccharide group may be selected from one or more of the following: a sialic acid, a modified sialic acid, a D-Glucose, a D-Galactose, a D-Mannose, an L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose. The one or more saccharide groups may be selected from one or more of the following: a sialic acid, a modified sialic acid, a β-D-Glucose, a β-D-Galactose, a β-D-Mannose, an α-L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose. The one or more saccharide groups may be selected from one or more of the following: a sialic acid, a modified sialic acid, a D-Glucose, a D-Galactose, a D-Mannose, an L-Fucose, or a Xylose. The one or more saccharide groups may be N-linked or O-linked. The compound may be further covalently bound to a protein. The glycoprotein may be mucin-linked. The glycoprotein may be asparagine-linked. The substituted phenol may be O-nitrophenyl.

The ester may be independently selected from one or more of the following: an acetate, a propionate, a butyrate, a pentanoate, a hexanoate, a heptanoate, a octanoate, a nonanoate, or a decanoate. The ester may be independently selected from one or more of the following: a linear acetate, a linear propionate, a linear butyrate, a linear pentanoate, a linear hexanoate, a linear heptanoate, a linear octanoate, a linear nonanoate, or a linear decanoate. The ester may be independently selected from one or more of the following: a branched acetate, a branched propionate, a branched butyrate, a branched pentanoate, a branched hexanoate, a branched heptanoate, a branched octanoate, a branched nonanoate, or a branched decanoate.

The modification of the protein ma enzymatic. The protein may be a protein therapeutic. The method may include contacting the sugar acceptor, the compound of Formula I or a pharmaceutically acceptable salt thereof, and an enzyme capable of transferring the compound of Formula I to the sugar acceptor, the contacting step taking place under conditions suitable for the transfer and covalent bonding to the compound of Formula I to the sugar acceptor.

The covalent bonding the compound of Formula I or a pharmaceutically acceptable salt thereof to the sugar acceptor may be carried out by synthetic chemical reaction.

The formation of the covalent conjugate with the compound of Formula I may modulate a biological property of the sugar acceptor or a therapeutic moiety comprising the sugar acceptor.

The therapeutic moiety may be a protein. The biological property may be resistance to enzymatic hydrolysis, biological stability or a pharmacokinetic property. The method may be an in vitro cell-free method.

The method may further include removing a terminal glycosyl group from a glycosylation structure to form the sugar acceptor group.

The glycosylation structure may be a glycoprotein or a glycolipid. The one or more saccharide groups may be N-linked or O-linked. G may be OMe, Me, OAc, —$CO_2R$, where R is H, $C_{1-7}$ alkyl, $C_{3-10}$ heterocyclyl or a $C_{5-20}$ aryl.

The one or more saccharide groups may be selected from one or more of the following: a sialic acid, a modified sialic acid, a glucose, a galactose, a mannose, a fucose, an acetylgalactosamine, an acetylglucosamine, an acetylgalactosamine thiazoline, an acetylglucosamine thiazoline, an acetylneuraminic acid, or a xylose. The sialic acid or modified sialic acid may be o-linked. The one or more saccharide groups may be selected from one or more of the following: a sialic acid, a modified sialic acid, a β-D-Glucose, a β-D-Galactose, a β-D-Mannose, an α-L-Fucose, a N-Acetylgalactosamine, a N-Acetylglucosamine, a N-Acetylgalactosamine thiazoline, a N-Acetylglucosamine thiazoline, a N-Acetylneuraminic acid, or a Xylose. The sialic acid or modified sialic acid may be o-linked.

X may be a sialic acid, a modified sialic acid, D-Glucose, D-Galactose, D-Mannose, L-Fucose, N-Acetylgalactosamine, N-Acetylgalactosamine thiazoline, N-Acetylglucosamine, N-Acetylglucosamine thiazoline, N-Acetylneuraminic acid, or Xylose. X may be a sialic acid, a modified sialic acid, β-D-Glucose, β-D-Galactose, β-D-Mannose, α-L-Fucose, N-Acetylgalactosamine, N-Acetylgalactosamine thiazoline, N-Acetylglucosamine, N-Acetylglucosamine thiazoline, N-Acetylneuraminic acid, or Xylose. The sialic acid or modified sialic acid may be o-linked.

BRIEF DESCRIPTION OF THE DRAWINGS

In drawings which illustrate embodiments of the invention:

FIG. 3A-E show an HPAEC-PAD analysis of free N-glycans released from untreated asialofetuin/fetuin and (7F)-sialylation of asialo-fetuin, with negative charge increasing from left to right, and with the bacterial sialyltransferases as noted. B, C and D show mutant PmST1 on the left panel and Cst-I on the right panel.

DETAILED DESCRIPTION

Figure 1A:
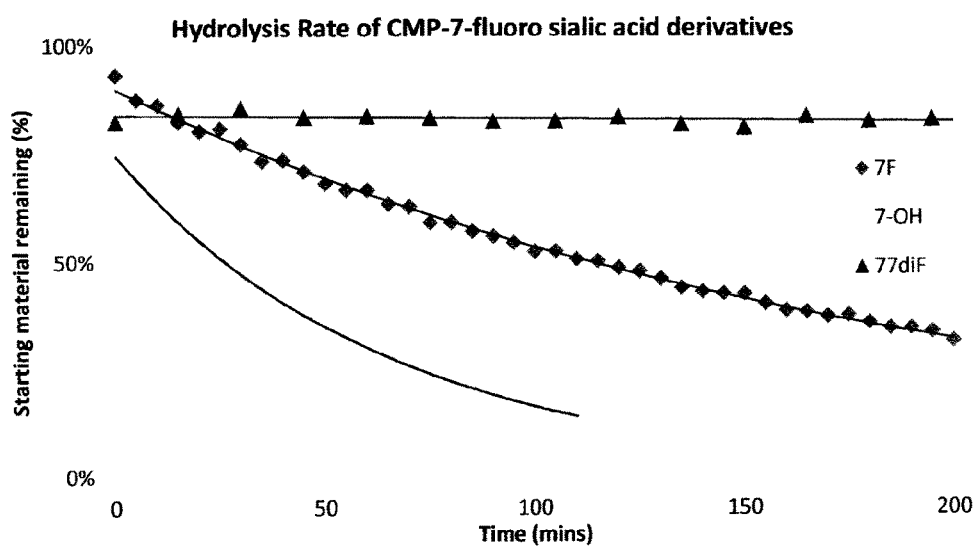
FIG. 1A shows a time course for hydrolysis of CMP 7-modified sialic acids, at pH 7.2 and 60° C.

Various alternative embodiments and examples are described herein. These embodiments and examples are illustrative and should not be construed as limiting the scope of the invention.

The maintenance of therapeutic glycoproteins within the circulatory system is associated, in large part, with the retention of sialic acids as terminal sugars. De-sialylation, either by spontaneous cleavage or through host sialidase action, leads to rapid protein clearance through the liver. The installation of minimally modified sialic acids that are resistant to cleavage, yet are biologically equivalent, is expected to increase circulatory half-lives and thus improve pharmacokinetic behaviour. Accordingly, there is a balance necessary between reduction of de-sialylation and maintenance of the biological function of the glycoprotein, when making a modification of the sialic acid. Described herein is the synthesis of CMP sialic acid derivatives (for example, bearing fluorine atoms at the 7-position) using a chemoenzymatic approach from the corresponding 4-deoxy-4-fluoro-GlcNAc derivatives. The CMP conjugates were tested as substrates for two different sialyltransferases and both were found to be capable of transferring the modified sugars to galactose-containing acceptors at rates only slightly reduced from that for the parent sugar. Using the *Campylobacter* sialyltransferase Cst-I sialyl galactosides bearing a chromogenic aglycone were synthesized and used as substrates to probe the effects of 7-deoxyfluorination on kinetic parameters for sialidases from the two GH families. Rate constants for spontaneous hydrolysis of these glycosides and of the CMP NeuNAc derivatives were also measured. A single fluorine at the 7-position dramatically reduced the efficiency of the family GH33 sialidases, but had little effect on cleavage by a viral neuraminidase from family GH34. Therefore, 7-Fluorosialylation specifically and carbon 7 modified sialic acids generally, offer considerable promise as a means of prolonging circulatory half-lives of therapeutic glycoproteins and glycolipids.

A "modified sialic acid" as described herein is described in Formulas I and II and by their precursors described in Formulas III and IV.

A number of routes could be envisaged by which sialic acids bearing these 7-position modifications could be incorporated into the glycoconjugates of interest. An example of one route could be that in which the glycoconjugate of interest is isolated from a suitable biological system and any sialic acid at the position of interest may be removed by sialidase action, if needed. The glycoconjugate of interest with the sialic acid removed may then be modified "in vitro" with the independently prepared 7-modified sialic acid as described herein. The 7-modified sialic acid may be prepared via chemoenzymatic synthesis of the CMP-7-fluorosialic acid and then transferred using a suitable sialyl transferase. In this case compounds of Formula I may be employed where G is CMP or some other activated leaving group compatible with stability of the donor sugar and usage by the transferase. An example might be a simple aryl sialoside, as shown previously ((2007) JCS Chem. Comm, 207, 365-367).

A second route may be one in which the isolated glycoconjugate is treated with an endo-glycosidase that removes an oligosaccharide fragment. This modified glycoconjugate could then be converted to the desired version containing the 7-modified sialic acid by chemoenzymatic preparation of the oligosaccharide of interest and then attached to the modified glycoconjugate using a suitable wild type or modified endo-glycosidase. An example of this would be the use of Endo-H to cleave N-glycans from proteins leaving a single GlcNAc residue at the point of attachment. This same enzyme, another such end-glycosidase, or an engineered version may then be used to re-attach an oligosaccharide via activation of the oligosaccharide typically as the oxazoline. In this case the reagent appended may be represented by Formula II wherein X is a galactose-terminated oligosaccharide of the desired structure, activated for transfer by the corresponding endo-glycosidase. An example might be the (7-fluorosialyl-α-2,3-Gal-β-1,4-GlcNAc-β-1,2-Man-α-1,6-Man)-α-1,6-Man-β-1,4GlcNAc (oxazoline).

A third route may be one in which the glycoconjugate of interest is produced in a cell-based system wherein the incorporation of the natural sialic acid is suppressed and the medium is supplemented by the modified sialic acid itself or with some pro-version that can more readily enter the cells and become converted to the free modified sialic acid then may be incorporated. In this case reagents of Formula III would be used wherein $M_{1-3}$ could be OH or a simple ester derivative. Likewise the cells could be supplemented with a suitably modified precursor to the 7-modified sialic acid such as 4-modified ManNAc or GlcNAc or a derivative thereof. This could be converted to the modified sialic acid within the cell by endogenous enzymes (natural or engineered in) and then incorporated as above. In this case reagents of Formula IV would be used wherein $Q_{1-3}$ could be OH or some simple ester derivative.

An "activated leaving group" as described herein refers to those moieties which are easily displaced in enzyme-regulated nucleophilic substitution reactions. Examples of such groups include, for example, fluoro, chloro, bromo, tosylate ester, mesylate ester, triflate ester and the like. One constraint on the activated leaving group, is that it should not sterically encumber the enzymatic transfer of the glycoside to the acceptor. Accordingly, activated glycoside derivatives may include glycosyl fluorides and glycosyl mesylates, with glycosyl fluorides being of particular interest. For example, alpha-sialyl fluoride or beta-sialyl fluoride.

As used herein, a "nucleoside phosphate" (including nucleoside mono-, di- or triphosphates) or analog thereof may be added to Formula I, wherein G=O-nucleoside phosphate. For example, nucleoside monophosphates may include, for example, adenosine monophosphate (AMP), cytidine monophosphate (CMP), uridine monophosphate (UMP), guanosine monophosphate (GMP), inosine monophosphate (IMP) and thymidine monophosphate (TMP). Nucleoside triphosphates may include adenosine triphosphate (ATP), cytidine triphosphate (CTP), uridine triphosphate (UTP), guanosine triphosphate (GTP), inosine triphosphate (ITP) and thymidine triphosphate (TTP). A nucleoside triphosphate may be UTP. Alternatively, the nucleoside phosphate may be a nucleoside diphosphate, for example, adenosine diphosphate (ADP), cytidine diphosphate (CDP), uridine diphosphate (UDP), guanosine diphosphate (GDP), inosine diphosphate (IDP) and thymidine diphosphate (TDP). Alternatively, an analog of the nucleoside phosphate may be used. Suitable analogs may include, for example, nucleoside sulfates and sulfonates. Still other analogs include simple phosphates, for example, pyrophosphate.

The different nucleoside phosphates be utilized as the entity that is ultimately added to the compounds (for example, —CMP) and as the entity that is part of the enzymatic reaction with the sialic acid synthase (for example, CMP sialic acid synthase with CTP being used as a substrate). Alternatively, other nucleoside tri-phosphates (for example, ATP, UTP, GTP, ITP, TTP) could be used to modify the compounds of Formula I (for example, to add an AMP, UMP, GMP, IMP, TMP to the compounds of Formula I). Furthermore, it may be possible for an enzyme to make use of the nucleoside di-phosphates (for example, CDP, ADP, UDP, GDP, IDP, TDP).

Currently known enzymes utilize the CTP to CMP conversion and derivatives thereof. Nevertheless, it is possible that an enzyme could be evolved or found that would work with different nucleoside phosphates.

In comparing cell based synthetic systems with in vitro synthetic systems, the compounds used will vary depending on the compounds being used (i.e. Formula I or Formula II). For example, the compounds of Formula I are more likely to be incorporated in a glycoprotein using a cell based system than would be the compounds of Formula II. However, both may be used in an in vitro method. In part, this is because it is less likely that a sugar chain of Formula II would be added a protein or lipid in a cell system. However, where protein is not glycosylated or partially glycosylated, an in vitro system may be useful in adding a sugar chain (i.e. for example, of Formula II) to the protein.

An "ester" as used herein is a carbonyl adjacent to an ether linkage. For example an ester may be selected from one or more of the following: acetate, propionate, butyrate, pentanoate, hexanoate, heptanoate, octanoate, nonanoate, decanoate, in all cases linear or branched. The esters may assist in getting the compounds (for example, of Formula I, III, or IV) into the cell where they may be hydrolysed before incorporation into the heterologous protein expressed by the cells of a cell based expression system. Accordingly, such esterified compounds of Formula I may be more suitable for cell based systems than in vitro systems.

A "therapeutic moiety" as used herein is meant to include any compound that may be used in the treatment of or the alleviation of symptoms associated with a disease or condition. Treatment includes the administration of a therapeutically effective amount of a compound capable of preventing or inhibiting a disease or condition, or alleviating symptoms associated with a disease or condition. A therapeutic moiety may be a therapeutic polypeptide or therapeutic protein.

Therapeutic proteins are known in the art (see for example, Leader et al.[79,80]). The vast majority of peptide therapeutics are injected. However, injection can be expensive (i.e. requiring someone skilled in administering the dose), and inconvenient, thus resulting in reduced compliance. Alternatively, intranasal delivery is an option for some peptide therapeutics.

The terms 'peptide', 'polypeptide' and protein' may be used interchangeably, and refer to a compound comprised of at least two amino acid residues covalently linked by peptide bonds or modified peptide bonds (for example, peptide isosteres). In particular, the therapeutic 'proteins' described herein may be coupled to the modified sialic acid derivatives described herein, such that circulatory half-lives may be improved. Any therapeutic protein may be modified as described herein, such that the modification may provide additional desired properties to the peptide (for example, increased half-life). The amino acids comprising a peptide or protein described herein may also be modified in other ways, such as post-translational processing, or by chemical modification techniques which are well known in the art.

Therapeutic protein expression systems as used herein refers to a cell or collection of cells that are capable of heterologous gene expression of a therapeutic protein. Therapeutic proteins have been expressed by a range of organisms (i.e. bacteria, yeast, mammalian cells and, transgenic plants and animals). A person of skill in the art would be able to select an expression system based on the properties of the therapeutic protein and the capabilities of a given expression system. For example, one or more of the following: (a) codon usage in the heterologous gene relative to the codon usage bias in the expression cell; (b) folding of heterologous protein; and (c) post-translational modifications (such as, glycosylation (see the more complete list below)); (d) toxicity of the heterologous protein to the expression cell; would likely be considered in deciding on a expression system.

Other examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, additional glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination, as known by persons skilled in the art.

Sialic acid negative (−) protein expression system refers to any cell that does not produce sialic acid. For example, the cell may be sialic acid negative due to a mutation in a biosynthetic pathway enzyme or a knock-out of such an enzyme (for example, hydrolyzing UDP-N-acetylglucosamine 2-epimerase or sialic acid synthase). Alternatively, the cell or cells may, for example, lack the ability to produce or obtain a necessary component of the sialic acid biosynthetic pathway. Such sialic acid negative cells, may be provided with a compound of Formula I or Formula II, such that the cells are able to produce therapeutic proteins having a modified sialic acid moiety, as described herein.

Alternatively, cells capable of producing sialic acid may be provided growth media that contains a modified precursor of sialic acid (for example, a compound of Formula III or Formula IV), such that the cells produce therapeutic proteins having a modified sialic acid moiety.

The ability to control glycosylation at defined sites represents a useful tool for engineering glycosylation structures. This can be done by making a "sugar acceptor" or "glycosyl acceptor" part of a glycosylation structure that may then react with a compound that is described herein.

A "glycosylation structure" as used herein is generally a saccharide and may further comprise a monoantennary structure, a biantennary structure, a triantennary structure, a glycoprotein, glycolipid, or a complex glycosylation structure. The structures disclosed herein may include naturally occurring or synthetic monosaccharides, oligosaccharides or polysaccharides, and may be used to modify N-linked or O-linked glycosylation structures. Where the glycosylation structure is a glycoprotein, the sugar acceptor may be covalently bound to a terminal or internal amino acid.

Furthermore, the glycosylation structure may include a linker group and/or other moieties (for example, one or more poly(alkylene glycol) molecules).

Sialic acid biosynthesis in mammals requires two main enzymes: (1) a hydrolyzing UDP-N-acetylglucosamine 2-epimerase, produces N-acetylmannosamine and UDP from UDP-N-acetylglucosamine; and (2) mammalian sialic acid synthase, produces N-acetylneuraminic acid 9-phosphate in a condensation reaction with phosphoenolpyruvate. Whereas, in some bacteria, there is also a hydrolyzing UDP-N-acetylglucosamine 2-epimerase, but a N-acetylneuraminic acid lyase can produce N-acetylneuraminic acid directly from pyruvate and N-acetylmannosamine.

A modified sialic acid, as described herein, may be attached to a sugar acceptor on a glycosylation structure via a variety of ways. Nevertheless, the modified sialic acid would be attached directly to Gal (in most cases) or to another sialic acid (in a very few cases).

For example, the attachment may be as follows:

Modified Sialic Acid—alpha-2,3-Gal—Either directly to protein or via other sugars;

Modified Sialic Acid—alpha-2,6-Gal—Either directly to protein or via other sugars; or Modified Sialic Acid—alpha-2,8-Sialic Acid—Either directly to protein or via other sugars.

7-carbon sialic acid modifications are described herein with regards to sialoside stability (for example, the 7-fluoro modified sialic acids). The 7-position is still close to the ring oxygen, where there is relative build up of positive charge in the transition state, thus substitution of the oxygen by a more electronegative fluorine, bromine, or chlorine atom, or where C7 is a carbonyl group, there should be a destabilising effect on the transition state 1. Furthermore the substitution of oxygen for fluorine, bromine, or chlorine, or where the C7 is a carbonyl group, would effectively remove a hydrogen bond donor, which may also affect the energy of any enzyme-catalyzed transition state if the interaction between the enzyme and the 7-OH is important in catalysis[35,36].

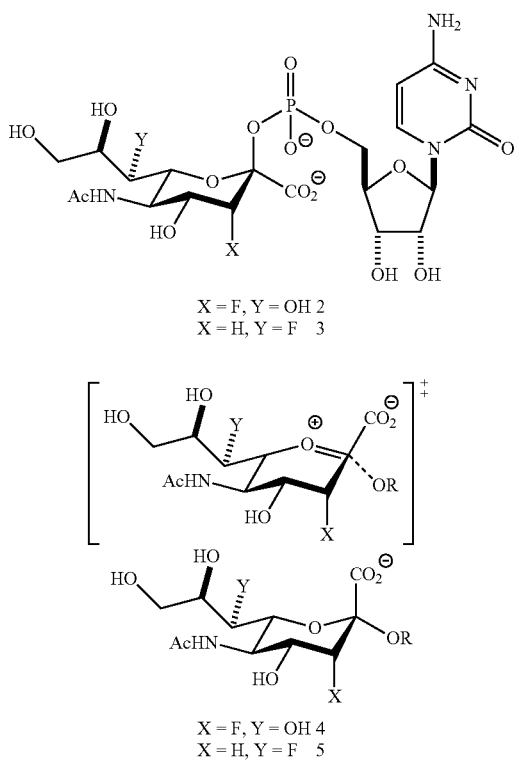

SCHEME 1 shows some fluorinated analogues of sialic acid and derivatives. 1 is the oxocarbenium ion transition state for the hydrolysis of CMP 3-fluoro sialic acid 2 and CMP 7-fluoro sialic acid 3. 4 and 5 are the 3-fluoro-sialoside and the 7-deoxy-7-fluoro sialoside.

Materials and Methods

All chemicals were of analytical grade purchased from the Sigma-Aldrich™ company unless otherwise stated. Analytical thin-layer chromatography (TLC) was performed on aluminium-backed sheets of Silica Gel 60F$_{254}$ (E. Merck™) of thickness 0.2 mm using a mobile phase mixture of ethyl acetate, methanol and water (7/2/1 v/v/v). The plates were visualised using UV light (254 nm) and/or by exposure to 10% ammonium molybdate (2 M in $H_2SO_4$) followed by charring. Flash column chromatography was carried out using Merck Kieselgel 60 (230-400 mesh). Ion-exchange chromatography was performed using Dowex® 1X2-200 resin (formate form) using an ammonium formate gradient (50 mM to 1 M). Reverse-phase silica gel chromatography was performed using Waters Sep-Pak® C18 cartridges with a water/acetonitrile gradient as specified. Size exclusion chromatography was performed using Bio-Rad Bio-Gel® P-2 column (22 mm×80 cm, 100-200 mesh), eluting with ammonium formate buffer (20 mM, pH 8.1) at a rate of 10 mL/hour. HPLC was performed using a Waters 600 multi-solvent delivery system (buffer A is acetonitrile, buffer B is 20 mM ammonium formate, pH 8.1) and Waters 2996™ photodiode array detector. Reverse phase silica gel HPLC was performed with a Phenomenex Jupiter C18™ reverse-phase column (10×250 mm) at a rate of 4 mL/min and a linear gradient (0-10% buffer A over 40 minutes) and regular phase silica gel HPLC was performed with TSKgel Amide-80 column (21.5×300 mm) at a rate of 6 mL/min and a linear gradient (20-70% buffer B over 40 minutes).

Proton and carbon NMR spectra were recorded on Bruker Avance™ 600inv Fourier Transform spectrometer fitted with a TCI-Z cryoprobe or Bruker Avance™ 400inv Fourier Transform spectrometer fitted with 5 mm BBI-Z probe. Fluorine and phosphorus NMR spectra were recorded on a Bruker Avance™ 300 fitted with a 5 mm QNP probe. All spectra are recorded using an internal deuterium lock and are referenced internally using the residual solvent peak. Carbon and proton chemical shifts are quoted in parts per million (ppm) downfield of tetramethylsilane, fluorine chemical shifts are quoted downfield of trifluoroacetic acid, phosphorus chemical shifts are quoted downfield of aqueous phosphoric acid. $^1$H, $^{13}$C, $^{19}$F and $^{31}$P chemical shifts are rounded to the nearest 0.1 ppm. Coupling constants (J) are given in Hertz (Hz) and are quoted to the nearest 0.5 Hz. Carbon NMR spectra were performed with broadband proton decoupling and were recorded with DEPT. $^1$H-NMR experiments performed in $D_2O$ solvent were recorded with a water suppression protocol. Complex $^1$H- and $^{13}$C-spectra were assigned on the basis of $^1$H, COSY, $^{13}$C, DEPT, $^1$H-$^{13}$C HMQC and $^1$H-$^{13}$C HMBC as appropriate.

Mass spectra were recorded on a Waters/Micromass LCT using electrospray ionisation (ESI) and recorded using Time-Of-Flight (TOF) method using methanol or 20% water in acetonitrile as solvent.

All enzymes were obtained from the Sigma-Aldrich™ company, with the exception of CMP-sialic acid synthase[70], Cst-I[71], Pmo118h[72], which were expressed and purified as previously described. The H. influenza H1N9 membrane paste was a kind gift from Dr. Martin Petric. The GlcNAc/ManNAc epimerase was a kind gift from bovine kidney.

Kinetic Assays

All sialyltransferase kinetic parameters were determined using a CMP release assay[73]. Cst-I kinetics were performed at 37° C. in HEPES pH 7.5 buffer (20 mM) containing sodium chloride (50 mM), manganese chloride (10 mM) and magnesium chloride (10 mM) at substrate concentrations from 0.1 to 2 mM. Pmo118h kinetic analyses were performed at 37° C. in HEPES pH 8.5 buffer (20 mM) containing sodium chloride (50 mM) and magnesium chloride (20 mM) at substrate concentrations from 0.02 to 1 mM.

The sialidase or neuraminidase kinetic parameters were determined using a β-galactosidase coupled assay by a similar method to that previously described[74-75]. The C. perfingens assays were performed at 37° C., in pH 6.7 phosphate buffer (20 mM) containing sodium chloride (50 mM), magnesium chloride (2 mM) and BSA (0.5 mg/ml). The T. rangelli assays were performed at 30° C., in phosphate pH 6.0 buffer (20 mM) containing sodium chloride (50 mM), magnesium chloride (2 mM) and BSA (0.5 mg/mL). The H. influenza assays were performed at 25° C. in pH 5.9 tris buffer (50 mM) containing calcium chloride (20 mM) and BSA (0.5 mg/mL). A continuous UV assay, using a Varian Cary-4000 UV-vis spectrophotometer, was used to monitor the release of the ortho-nitrophenolate at 410 nm (ε=3800 $M^{-1}$ $cm^{-1}$). In brief, the substrate (0.1 to 2 mM) was incubated for 10 minutes in the desired buffer (190 μL total volume) containing β-galactosidase (0.04 Units), before the assay was initiated by the addition of a small (<10 µL) volume of the sialidase (variable concentrations). A stopped fluorescence assay, using a Cary Eclipse fluorescence spectrophotometer, was used to monitor the release of methylumbelliferyl alcohol ($\lambda_{ex}$=365 nm, $\lambda_{emit}$=450 nm, ε=2150 µM$^{-1}$ cm$^{-1}$ at pH 10 and 700 v). In brief, three identical assays were set up that contained the substrate (0.1 to 5 mM), and were incubated in the desired buffer (total volume=16 µL) containing β-galactosidase (0.05 Units). The assay was initiated by the addition of the sialidase (4 µL, variable concentration) and immediately an aliquot (4 µL) was removed and diluted into CAPS buffer (20 mM, pH 10.0, 996 µL) for measurement of the fluorescence of the released coumarin. Three more aliquots were taken at set time intervals (between 1 and 5 minutes), giving a total of four data points and these were plotted to give an initial reaction rate at each concentration. Assays at each substrate concentration were repeated in triplicate to give an averaged reaction rate. These data were analysed using GraFit from Erithacus software.

Measurement of Rate of Hydrolysis of CMP 7-Modified Sialic Acids, by $^1$H-NMR

CMP 7-modified sialic acid was dissolved in deuterated phosphate buffer (10 mM, pH 7.2, 700 µL) containing sodium chloride (100 mM) to give a final substrate concentration of 2 mM. The mixture was equilibrated to 600° C. for 10 minutes in the NMR spectrometer before spectra were acquired (32 scans each using water suppression pulse sequence) at 5 or 15 minute time intervals. The intensity of the signals corresponding to the H3$_{eq}$ and H3$_{ax}$ ring protons, and the H4-proton of the cytosine ring were measured, since these three showed a significant chemical shift between CMP-conjugate and the free hydrolysed CMP. These intensities were normalized with respect to the intensity of the total H5-cytosine peak, and were plotted as a function of time and fitted to a single exponential using the program GraFit from Erithacus software. The exponentials obtained for each of the three diagnostic protons were averaged, and the experiment was repeated to ensure consistency.

Measurement of Rate of Hydrolysis of 7-Modified Sialyl-Galactose Conjugates, by $^1$H-NMR The 4-methylumbelliferyl-7-modified sialyl-galactoside conjugate was dissolved in a mixture of D$_2$O and hydrochloric acid (25 mM final concentration of HCl, 700 µL) containing sodium chloride (250 mM) to give a final substrate concentration of 2 mM. The mixture was equilibrated at 600° C. for 10 minutes in the NMR spectrometer before spectra were acquired (32 scans each using water suppression pulse sequence) at 5 or 15 minute time intervals. The intensities of the signals corresponding to the anomeric proton of the galactose (H1') and the H3-equatorial proton (H3"$_{eq}$) of the sialic acid were measured, since these showed a significant chemical shift between sialyl-galactose conjugate and the free sialic acid. These intensities were normalized with respect to the intensity of the total H4-coumarin peak, and were plotted as a function of time and fitted to a single exponential using the program GraFit. The exponentials obtained for the two diagnostic protons were averaged, and the experiment was repeated to ensure consistency.

General Syntheses of 7-Deoxy-7-Fluoro Sialic Acids Using Epimerase/Aldolase Two Enzyme System.

4-Deoxy-4-modified GlcNAc derivatives[76] (1 eq.) and sodium pyruvate (5 eq.) were dissolved in water to give a final sugar concentration of 100 mM. The GlcNAc/ManNAc epimerase (0.2 U/µmol) and sialic acid aldolase (2 U/µmol) were added and the mixture was incubated at 37° C. for 48 hours. The mixture was centrifuged (10,000 rpm) for 5 minutes and the supernatant was loaded directly onto a pre-equilibrated (50 mM ammonium formate) ion-exchange column. The column was washed (20 mL, 50 mM ammonium formate) to elute any starting materials. The products were eluted from the column (20 mL, 1 M, ammonium formate), and crude product-containing fractions, as identified by TLC (mobile phase of ethyl acetate/methanol/water/acetic acid in a 4:2:1:0.1 ratio), were pooled and lyophilized. Purification was achieved by regular-phase HPLC (as described above), with the products eluting at around 45% buffer B, with the product-containing fractions identified by UV (N-acetyl absorbs at 198 nm) and TLC before being pooled and lyophilised to yield pure product.

General Syntheses of CMP 7-Deoxy-7-Fluoro Sialic Acids

7-Deoxy-7-fluoro sialic acid derivative (1 eq.) and CTP disodium salt (1.05 eq.) were dissolved in Tris buffer (100 mM, pH 8.5) containing magnesium chloride (20 mM) and DTT (0.1 mM) to give a final sialic acid concentration of 15 mM. CMP-sialic acid synthetase (1 U/µmol) and inorganic pyrophosphatase (1 U/mmol) were added and the mixture was tumbled at ambient temperature. The pH of the solution was checked regularly and aqueous sodium hydroxide solution (1 M) was added as appropriate to keep the pH constant. On completion of reaction, as observed by TLC analysis (ethyl acetate/methanol/water/concentrated ammonia solution in a 4:3:2:1 ratio mobile phase), the mixture was cooled to −80° C. Once it had thawed it was filtered (0.44 µm) and incubated with alkaline phosphatase (20 U/mmol) for 10 minutes. The mixture was filtered (0.44 µm) again and loaded directly onto an ion-exchange column that had been pre-equilibrated with ammonium formate (50 mM). After an initial wash using the same buffer, a stepped gradient (50 mM to 1 M) was performed and product-containing fractions were identified by TLC, pooled and lyophilised. This crude product was dissolved in the minimum volume of buffer (20 mM ammonium formate buffer, pH 8.1) and loaded onto a size exclusion column. The column was run at 10 mL/hour and fractions were collected every 15 minutes. Product-containing fractions were identified by TLC analysis, pooled and lyophilised.

General Synthesis of 7-Deoxy-7-Fluoro Sialyl Galactosides

The aryl galactoside acceptor (1.2 eq.) was incubated with the CMP 7-modified sialic acid (1.0 eq.) donor in HEPES (50 mM, pH 7.5) buffered solution containing manganese chloride (10 mM) in the presence of Cst-I (65 µM) and alkaline phosphatase (300 U/mL) at room temperature. On completion of reaction, as observed by TLC analysis (ethyl acetate/methanol/water, in a 7:2:1 ratio mobile phase), the mixture was filtered (0.44 µm) and loaded onto a pre-equilibrated Waters SepPak C18 (2 g) column, washed with water (10 column volumes) and products eluted with 5% acetonitrile in water. Product-containing fractions were identified by TLC, pooled and lyophilised. Further purification was performed using reverse-phase HPLC as described above, with products eluting at around 7% buffer A.

5-Acetamido-3,5,7-trideoxy-7-fluoro-D-glycero-β-D-galacto-2-nonulopyranosidic acid ammonium salt (9)

4-Deoxy-4-fluoro GlcNAc[76] 6 (220 mg, 0.94 mmol) and sodium pyruvate (519 mg, 4.72 mmol) were combined in buffered solution (total volume=9.4 mL) as described in General Synthesis. The 7-deoxy-7-fluoro sialic acid (266 mg, 0.86 mmol, 91%) was obtained as a white solid with identical physical data to that previously reported[77].

5-Acetamido-3,5,7-trideoxy-7,7-difluoro-D-glycero-D-galacto-2-nonulopyranosidic acid ammonium salt (11)

4-Deoxy-4,4-difluoro GlcNAc[76] 8 (100 mg, 0.41 mmol) and sodium pyruvate (225 mg, 2.05 mmol) were combined in buffered solution (total volume=4.1 mL) in the procedure described in General Synthesis. The 7-deoxy-7,7-difluoro sialic acid (68 mg, 0.21 mmol, 51%) was obtained as a white solid as a 2:1 mixture of b:a anomers.

$d_H$ (400 MHz $D_2O$) 1.75 (2H, dd, J 13.5 and 12.5, a- and b-H3ax), 1.83 (1H, dd, J 13.5 and 5.0, b-H3eq), 1.88 (3H, s, a-Ac), 1.92 (3H, s, b-Ac), 2.08 (1H, dd, J 13.5 and 4.5, a-H3eq), 3.54 (1H, dd, J 12.0 and 7.5, a-H9a), 3.56 (1H, dd, J 12.0 and 7.5, b-H9a), 3.73 (1H, dd, J 12.0 and 3.0, b-H9b), 3.75 (1H, ddd, J 12.0, 2.5 and 1.5, a-H9b), 3.92-3.84 (3H, m, a-H4, a-H5 and b-H8), 4.01 (1H, ddd, J 23.0, 7.5 and 3.0, a-H8), 4.10 (1H, ddd, J 12.0, 5.0 and 4.0, b-H4), 4.14 (1H, ddd, J 21.5, 9.0 and 3.0, a-H6), 4.40 (1H, dd, J 18.5 and 3.5, b-H6), 4.44 (1H, d, J 4.0, b-H5);

$d_C$ (100 MHz $D_2O$) 21.4 (b-COMe), 21.6 (a-COMe), 34.3 (b-C3), 38.4 (a-C3), 46.8 (b-C5), 50.2 (a-C5), 59.3 (a- and b-C9), 64.4 (b-C4), 66.6 (a-C4), 66.8 (dd, J 33.5 and 20.5, b-C6), 67.6 (dd, J 28.5 and 24.0, a-C6), 68.8 (dd, J 31.0 and 23.0, a-C8), 69.0 (dd, J 28.5 and 22.0, b-C8), 95.9 (a-C2), 96.3 (b-C2), 120.4 (dd, J 254.5 and 248.0, b-C7), 121.5 (dd, J 249.0 and 252.5, a-C7), 173.8 (CO), 174.3 (CO), 175.1 (CO), 175.3 (CO);

$d_F$ (282 MHz $D_2O$) −121.0 (1F, ddd, J 262.5, 21.5 and 1.5, a-7a), −122.9 (1F, ddd, J 262.5, 23.0 and 4.5, a-7b), −123.0 (1F, ddd, J 263.0, 18.5 and 7.0, b-7a), −124.1 (1F, ddd, J 263.0, 17.5 and 3.5, b-7b);

HRMS calc for $C_{11}H_{16}NO_8F_2$ (M-H) is 328.0844, found 328.0848 (+1.2 ppm)

5-Acetamido-3,5,7-trideoxy-2-(hydrogen 5'-cytidylate)-7-fluoro-D-glycero-b-D-galacto-2-nonulopyranosidic acid diammonium salt (14)

Acid 9 (120 mg, 0.39 mmol) was combined with cytidine triphosphate (214 mg, 0.41 mmol) and dithiothreitol (1 mg) in a buffered solution (total volume of 24.4 mL) with CMP-sialic acid synthetase and inorganic pyrophosphatase in the procedure described in General Synthesis. After purification the CMP 7-deoxy-7-fluoro conjugate 14[77] was obtained as a white solid (207 mg, 0.34 mmol, 86%);

$d_H$ (400 MHz $D_2O$) 1.55 (1H, ddd, J 13.0, 11.5 and 5.5, H3ax), 1.94 (3H, s, Ac), 2.41 (1H, dd, J 13.0 and 4.5, H3eq), 3.55 (1H, ddd, J 12.5, 5.0 and 2.0, H9a'), 3.71 (1H, dt, J 12.5 and 3.0, H9b'), 3.76-4.04 (9H, m), 4.33 (1H, dd, J 45.5 and 9.5, H7'), 5.86 (1H, d, J 4.5, H1), 6.00 (1H, d, J 7.5, m-Ar), 7.85 (1H, d, J 7.5, pAr);

$d_P$ (162 MHz $D_2O$) −4.3 (s);

$d_F$ (282 MHz $D_2O$) −206.7 (ddd, J 45.5, 29.5 and 2.0);

HRMS calc for $C_{20}H_{29}N_4O_{15}FP$ (M-H) is 615.1351, found 615.1343 (−1.3 ppm).

5-Acetamido-3,5,7-trideoxy-2-(hydrogen 5'-cytidylate)-7,7-difluoro-D-glycero-b-D-galacto-2-nonulopyranosidic acid diammonium salt (15)

Acid 11 (9.8 mg, 29.8 mmol) was combined with cytidine triphosphate (17.3 mg, 32.8 mmol) and dithiothreitol (1 mg) in a buffered solution (total volume of 1.99 mL) with CMP-sialic acid synthetase and inorganic pyrophosphatase in the procedure described in General Synthesis. After purification the CMP 7-deoxy-7,7-difluoro conjugate 15 was obtained as a white solid (12.0 mg, 18.5 mmol, 62%);

$d_H$ (400 MHz $D_2O$) 1.56 (1H, ddd, J 13.0, 11.0 and 5.5, H3ax), 1.87 (3H, s, Ac), 2.39 (1H, dd, J 13.0 and 3.0, H3eq), 3.25 (1H, dd J 12.0 and 8.0, H9a), 3.75 (1H, dt, J 12.0 and 2.0, H9b), 3.88-4.28 (9H, m), 5.85 (1H, d, J 4.5, H1), 5.99 (1H, d, J 7.5, m-Ar), 7.86 (1H, d, J 7.5, p-Ar);

$d_P$ (162 MHz $D_2O$) −4.5 (s);

$d_F$ (282 MHz $D_2O$) −121.7 (1F, dd, J 260.5 and 21.5, F7a), −125.4F, dd, J 260.5 and 25.5, F7b);

HRMS calc for $C_{20}H_{28}N_4O_{15}F_2P$ (M-H) is 633.1257, found 633.1265 (+1.3 ppm).

ortho-Nitrophenyl (5-Acetamido-3,5-dideoxy-D-glycero-α-D-galacto-non2-ulopyranosylonic acid)-(2→3)-β-D-galactopyranoside (17)

Ortho-nitrophenyl-b-D-galactopyranoside (7.5 mg, 25.0 mmol) was combined with CMP-sialic acid (19.1 mg, 30.0 mmol) in a buffered solution (total volume of 5.0 mL) with Cst-I and alkaline phosphatase according to the procedure described in General Synthesis. After isolation and purification the disaccharide 17 was obtained as a white solid (11.1 mg, 18.7 mmol, 75%);

$d_H$ (400 MHz $D_2O$) 1.69 (1H, t, J 12.0, H3"ax), 1.90 (3H, s, COMe), 2.65 (1H, dd, J 12.0 and 4.5, H3"eq), 3.45 (1H, dd, J 7.0 and 2.0, H7"), 3.50 (1H, dd, J 11.5 and 5.5, H9a"), 3.51 (1H, dd, J 10.0 and 1.5, H6"), 3.61-3.64 (2H, m, H6a' and H6b'), 3.67-3.79 (5H, m, H2', H5', H5", H8", H9b"), 3.90 (1H, d, J 3.0, H4'), 4.09 (1H, dd, J 9.5 and 3.0, H3'), 5.15 (1H, d, J 8.0, H1'), 7.13 (1H, t, J 7.5, H4-Ar), 7.31 (1H, d, J 8.5, H6-Ar), 7.56 (1H, dd, J 7.5 and 2.0, H5-Ar), 7.81 (1H, dd, 8.5 and 2.0, H3-Ar);

$d_C$ (100 MHz $D_2O$) 22.2 (COMe), 39.8 (C3"), 51.9 (C5"), 60.8 (C6'), 62.8 (C9"), 67.5 (C4'), 68.3 (C7"), 68.5 (C4"), 68.9 (C2'), 72.0 (C8"), 73.0 (C6"), 75.6 (C5'), 75.6 (C3'), 100.1 (C2"), 101.0 (C1'), 117.7 (C6-Ar), 123.2 (C4-Ar), 125.8 (C5-Ar), 135.3 (C3-Ar), 140.1 (C2-Ar), 149.6 (C1-Ar), 174.0 (CO), 175.2 (CO);

HRMS calc for $C_{23}H_{32}N_2O_{16}Na$ (M+Na) is 615.1650, found 615.1638 (−1.9 ppm).

ortho-Nitrophenyl (5-Acetamido-3,5,7-trideoxy-7-fluoro-D-glycero-α-D-galacto-non2-ulopyranosylonic acid)-(2→3)-β-D-galactopyranoside (18)

ortho-Nitrophenyl-b-D-galactopyranoside (5.7 mg, 18.8 mmol) was combined with CMP 7-deoxy-7-fluoro-sialic acid 14 (10.2 mg, 15.7 mmol) in a buffered solution (total volume of 3.14 mL) with Cst-I and alkaline phosphatase according to the procedure described in General Synthesis. After isolation and purification the disaccharide 18 was obtained as a white solid (6.0 mg, 10.0 mmol, 64%);

$d_H$ (600 MHz $D_2O$) 1.75 (1H, t, J 12.5, H3"ax), 1.92 (3H, s, COMe), 2.66 (1H, dd, J 12.5 and 4.5, H3"eq), 3.56 (1H, ddd, J 12.5, 6.5 and 1.5, H9"a), 3.59 (1H, ddd, J 12.5, 10.0 and 4.5, H4"), 3.64-3.67 (2H, m, H6'a and H6'b), 3.71 (1H, dd, J 29.0 and 10.5, H6"), 3.72 (1H, dt, J 12.5 and 2.5, H9"b), 3.78-3.80 (1H, m, H5'), 3.79 (1H, dd, J 10.0 and 8.0, H2'), 3.82 (1H, t, J 10.0, H5"), 3.93 (1H, d, J 3.0, H4'), 3.97 (1H, dtd, J 8.5, 6.5 and 2.5, H8"), 4.10 (1H, dd, J 10.0 and 3.0, H3'), 4.39 (1H, dd, J 48.0 and 9.0, H7"), 5.19 (1H, d, J 8.0, H1'), 7.16 (1H, t, J 8.0, H4-Ar), 7.33 (1H, d, J 8.5, H6-Ar), 7.56 (1H, ddd, J 8.5, 8.0 and 1.5, H5-Ar), 7.84 (1H, dd, 8.0 and 1.5, H3-Ar);

$d_C$ (150 MHz D$_2$O) 21.6 (COMe), 38.8 (C3"), 50.6 (C5"), 60.0 (C6'), 61.4 (C9"), 67.0 (C4'), 67.6 (C4"), 68.2 (C2'), 68.4 (d, J 27.5, C8"), 71.1 (d, J 18.5, C6"), 74.9 (C5'), 75.3 (C3'), 88.0 (d, J 180.0, C7"), 99.8 (C2"), 100.3 (C1'), 116.9 (C6-Ar), 122.5 (C4-Ar), 125.1 (C5-Ar), 134.7 (C3-Ar), 139.3 (C2-Ar), 149.0 (C1-Ar), 173.0 (CO), 174.2 (CO);

$d_F$ (282 MHz D$_2$O) −208.5 (ddd, J 48.0, 29.0 and 6.5);

HRMS calc for $C_{23}H_{30}N_2O_{15}F$ (M-H) is 593.1630, found 593.1635 (+0.8 ppm).

4-Methylumbelliferyl (5-acetamido-3,5-dideoxy-D-glycero-α-D-galacto-non2-ulopyranosylonic acid)-(2→3)-β-D-galactopyranoside (19)

4-Methylumbelliferyl b-D-galactopyranoside (3.4 mg, 10.1 mmol) was dissolved in DMSO (50 mL) and carefully diluted into a buffered solution (total volume of 1.68 mL) containing CMP-sialic acid (6.5 mg, 10.1 mmol) with Cst-I and alkaline phosphatase according to the procedure described in General Synthesis. After isolation and purification the disaccharide 18 was obtained as a white solid (4.1 mg, 6.6 mmol, 65%), with identical physical data to those previously reported[78].

4-Methylumbelliferyl (5-acetamido-3,5,7-trideoxy-7-fluoro-D-glycero-α-D-galacto-non2-ulopyranosylonic acid)-(23)-β-D-galactopyranoside (20)

4-Methylumbelliferyl b-D-galactopyranoside (3.5 mg, 10.5 mmol) was dissolved in DMSO (50 mL) and carefully diluted into a buffered solution (total volume 1.75 mL) containing CMP 7-deoxy-7-fluoro-sialic acid 14 (5.6 mg, 8.7 mmol) with Cst-I and alkaline phosphatase according to the procedure described in General Synthesis. After isolation and purification the disaccharide 20 was obtained as a white solid (2.8 mg, 4.4 mmol, 51%);

$d_H$ (600 MHz D$_2$O) 1.77 (1H, t, J 12.5, H3"ax), 1.93 (3H, s, COMe), 2.35 (3H, s, Ar-Me), 2.67 (1H, dd, J 12.5 and 4.5, H3"eq), 3.56 (1H, dd, J 11.5 and 5.5, H9a"), 3.61 (1H, ddd, J 12.5, 11.0 and 4.5, H4"), 3.66-3.69 (2H, m, H6a' and H6b'), 3.72 (1H, dd, J 11.5 and 2.0, H9b"), 3.73 (1H, dd, J 29.0 and 10.5 (1H6"), 3.79 (1H, dd, J 10.0 and 8.0, H2'), 3.81-3.85 (2H, m, H5' and H5"), 3.96 (1H, d, J 3.0, H4'), 3.99 (1H, dddd, J 9.0, 7.0, 5.5 and 2.5, H8"), 4.14 (1H, dd, J 10.0 and 3.0, H3'), 4.40 (1H, dd, J 46.5 and 9.0, H7"), 5.17 (1H, d, J 8.0, H1'), 6.17 (1H, s, H3-Ar), 7.02 (1H, d, J 2.0, H9-Ar), 7.05 (1H, dd, J 9.0 and 2.0, H7-Ar), 7.65 (1H, d, J 9.0, H6-Ar); $d_C$ (150 MHz D$_2$O) 18.4 (Ar-Me), 22.5 (COMe), 39.7 (C3"), 51.6 (C5"), 61.0 (C6'), 62.4 (C9"), 67.9 (C4'), 68.5 (C4"), 69.2 (C2'), 69.4 (d, J 27.5, C8"), 72.1 (d, J 17.0, C6"), 75.7 (C5'), 76.2 (C3'), 88.9 (d, J 180.0, C7") 100.3 (C1'), 100.6 (C2"), 104.0 (C9-Ar), 111.7 (C3-Ar), 114.3 (C7-Ar), 115.8 (C5-Ar), 127.1 (C6-Ar), 154.4 (C10-Ar), 156.8 (C4-Ar), 159.8 (C8-Ar), 165.2 (C2-Ar), 173.8 (CO), 175.2 (CO);

$d_F$ (282 MHz D$_2$O) −208.6 (ddd, J 46.5, 29.0 and 7.0);

HRMS calc for $C_{27}H_{33}NO_{15}F$ (M-H) is 630.1834, found 630.1818 (−2.6 ppm).

Several synthetic routes for the 7-ketosialic acid derivatives would be apparent to those skilled in the art, as illustrated synthetic scheme below.

SCHEME 2-Proposed chemoenzymatic synthesis of 7-ketosialic.

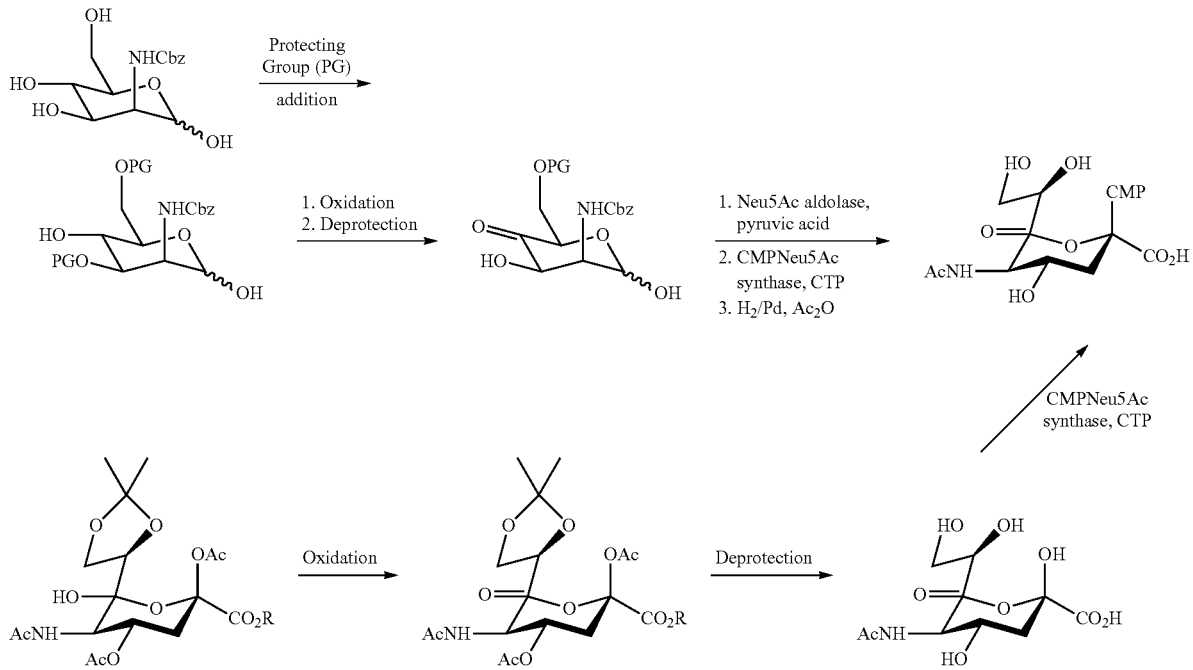

Enzymatic Protein Sialylation.

Fetuin (Sigma Aldrich™) or asialofetuin (Sigma Aldrich™, grade I) were dissolved in water to 10-20 mg/ml and purified by FPLC-SEC (Superdex 200™, 16×450 mm, flow 1 ml/min) with 20 mM HEPES, 500 mM NaCl, pH 7.5 at room temperature as running buffer. Pure fractions of monomeric protein were pooled, concentrated and stored at 4° C. until use. Sialylation reactions were performed enzymatically by using either a mammalian sialyltransferase (EXAMPLE 8) or a bacterial enzyme (EXAMPLE 9). The final reaction mixture contained either 100 mM ammonium bicarbonate buffer or 50 mM HEPES (pH 7.5), 10 mM MgCl$_2$, asialofetuin or fetuin (1-4.8 mg/ml), plus sialyltransferase as indicated. In order to prevent inhibitory and adverse action of free CMP and residual protease activity, bovine alkaline phosphatase (Sigma Aldrich™) and 1× complete protease inhibitor mix (EDTA-free, Roche™) were added. The donor sugar (CMP-SA or CMP-7FSA, respectively) was added to a final concentration of 15 mM, while negative control contained neither. In order to study the influence of inert macromolecules on reactions, all reactions were performed in the presence or absence of dextran-40. The reactions were incubated at 37° C. for the indicated times and analyzed by reducing SDS-PAGE (4-12% Bolt gels, MES running buffer, 5 μg fetuin loaded per lane).

Protein Sample Purification.

The sialyltransferase was removed from the solution by binding to Ni-NTA agarose beads pre-equilibrated with 100 mM ammonium bicarbonate buffer, 10 mM imidazole, pH 7.8 (50 μl beads/100 μl sample). Suspensions were incubated 30' at ambient temperature, spun and washed twice with buffer containing 20 mM imidazole. Combined material was concentrated and buffer exchanged to 5 mM ammonium bicarbonate buffer, pH 7-5 with an Amicon-4. Finally, all material was stored at −20° C.

Enzymatic N-glycan Release and Work-Up.

N-Glycans were released from the glycoprotein using glycerol-free PNGase F (NEB P0709) according to the user manual and solutions were concentrated using a Speedvac™. N-glycans were isolated and purified with graphitized carbon cartridges (100 mg, bondElut™, Agilent™) as follows. After activation with 5 ml MeOH and equilibration with 15 ml 0.1% TFA samples were dissolved in 1 ml of 0.1% TFA, and applied to the cartridges and then washed with 15 ml 0.1% TFA. Purified N-glycans were eluted with 2×1 ml of 25% MeCN in 0.1% TFA, then frozen and freeze-dried overnight.

High-pH Anion Exchange Chromatography with PAD Detection (HPAEC-PAD)

Non-permethylated samples were dissolved in 25 μl H$_2$O, spun at 17000×g and 10 μl of this cleared solution was injected for analytical separation. Gradient: Each run was started isocratic with 20 mM NaOAc in 100 mM NaOH for 5 min and NaOAc concentration was then increased over 55 min to 150 mM NaOAc. Flow rate was kept constant at 0.5 ml/min.

EXAMPLES

Example 1—Scheme 3

In order to make sialic acids fluorinated at the 7-position a chemoenzymatic approach was taken similar to those previously published for other derivatives[38, 39]. These routes use a commercially available sialic acid aldolase, which couples N-acetyl mannosamine (ManNAc) with pyruvate to yield sialic acid. Thus ManNAc derivatives fluorinated at the 4-position can be converted directly to 7-deoxy-7-fluoro sialic acid derivatives. This enzymatic approach circumvents the need to chemically manipulate the 7-position of sialic acid, which is the most difficult to manipulate and the least reactive of the sialic acid hydroxyl groups[40]. Where this approach differs from previous reports is in the use of the corresponding 4-fluoro glucosamine (GlcNAc) derivatives in the presence of a bacterial GlcNAc to ManNAc epimerase, along with the sialic acid aldolase to obtain the 7-deoxy-7-fluoro sialic acid derivatives, i.e. a two-enzyme one-pot conversion. By using these two enzymes the GlcNAc derivative is converted, by the epimerase, to the corresponding ManNAc derivative in situ (SCHEME 3), which then serves as a substrate for the aldolase. The chemical synthesis of such modified GlcNAc derivatives[41] is far more concise than that of the corresponding ManNAc configured sugars[42]. One drawback could be an impaired activity of the epimerase with 4-modified GlcNAc derivatives as substrates resulting in an insufficient flux to allow a viable synthetic route when used in tandem with the aldolase. However, recent reports with unmodified GlcNAc have shown that the epimerase/aldolase two-enzyme one-pot system is a viable route to make sialic acid on a commercial scale[43].

SCHEME 3-Chemoenzymatic synthesis of 7-deoxy-7-fluoro sialic acid derivatives. 4-Modified GlcNAc derivatives (100 mM), sodium pyruvate (500 mM), epimerase (0.1 U/μmol), aldolase (1U/μmol), 35° C., 48 h.

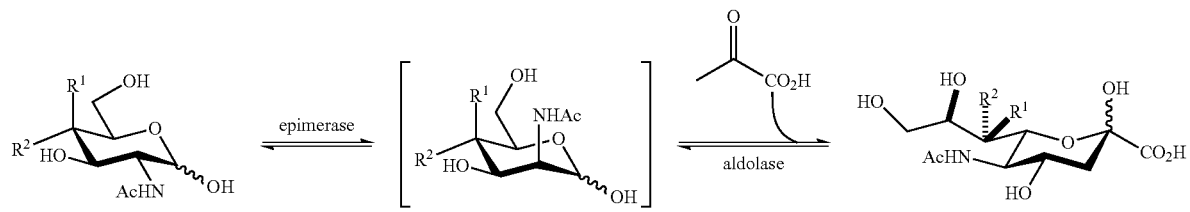

TABLE 1

Yields of 7-modified sialic acid derivatives (6, 7, and 8) using the epimerase/aldolase system;
[a]conversion, as measured by $^{19}$F-NMR; [b]yield = isolated yield.

| R$^1$ | R$^2$ | Substrate | NeuNAc | Conv (%)[a] | Yield (%)[b] |
|---|---|---|---|---|---|
| H | F | 6 | 9 | >95 | 91 |
| F | H | 7 | 10 | 19 | N/A |
| F | F | 8 | 11 | 66 | 51 |

4-Deoxy-4-fluoro GlcNAc 6, 4-deoxy-4-fluoro GalNAc 7 and 4-deoxy-4,4-difluoro GlcNAc 8 were synthesised on a 100-400 mg scale by a concise, divergent route, from a common precursor as has been previously described[41]. Each of these 4-modified sugars was tested as a substrate for the two-enzyme (epimerase and aldolase) one-pot conversion to 7-modified sialic acids in the presence of five equivalents of pyruvate. These conditions were used in an attempt to drive the reaction towards the desired sialic acid product, and each reaction was readily monitored by 19F-NMR over a 48 hour period. In each case the conversion shown in TABLE 1 is based on the ratio of GlcNAc and ManNAc substrates to NeuNAc products present in the reaction mixture, and the yield shown is the isolated yield of a scaled-up reaction after ion-exchange chromatography and regular-phase HPLC.

In the case of 4-deoxy-4-fluoro GlcNAc 6, almost complete conversion was observed after 24 hours in the presence of the two enzymes and the isolated yield of 7-fluoro sialic acid 9 of the scaled up reaction was excellent. Unfortunately, the corresponding GalNAc compound 7 showed minimal conversion, even over extended time periods. Consequently the sialic acid derivative 10, possessing the opposite stereochemistry to that of the natural compound at the 7-position, was not pursued further, but could still be made with lower expected yields using this chemoenzymatic synthesis. However, somewhat surprisingly, the 4,4-difluoro derivative 8 underwent good conversion to the 7,7-difluoro sialic acid derivative 11 and could be isolated in moderate yield. These three results indicate a requirement for an electronegative atom (oxygen or fluorine) in the equatorial position at the 4-position ($R^2$ of the precursor 4-modified GlcNAC). In the absence of this atom the yield of the sialic acid product drops dramatically. This limitation most likely resides in the aldolase since peaks corresponding to the TalNAc derivative were observed in the 19F-NMR spectrum of the reaction mixture of 7, indicating that the epimerase was converting the GalNAc starting material, but that the aldolase did not convert it efficiently to sialic acid product 10.

Example 2—Scheme 4

In order to assess the effect of deoxy-fluorination at the 7-position of sialic acid on sialidase activity a suitable substrate and associated kinetic assay were required. An attractive coupled assay that has previously been used to monitor the activity of a trans-sialidase from *T. cruzi*,[44] as well as to evaluate sialidase substrate specificities (SCHEME 4)[45,46] involved a NeuNAc-α-2,3-Gal-β-O-Aryl glycoside 12 substrate. In the presence of a sialidase the sialic acid is cleaved, liberating an aryl β-galactoside 13, whose formation can be readily monitored by inclusion of a β-galactosidase. Liberation of the phenol(ate) product, by action of the β-galactosidase, can be followed by UV/Vis or fluorescence spectroscopy. In order to ensure that galactoside cleavage was not rate-limiting, the commercially available *E. coli* lac Z β-galactosidase was used since it has a high activity and a wide pH operating range[47].

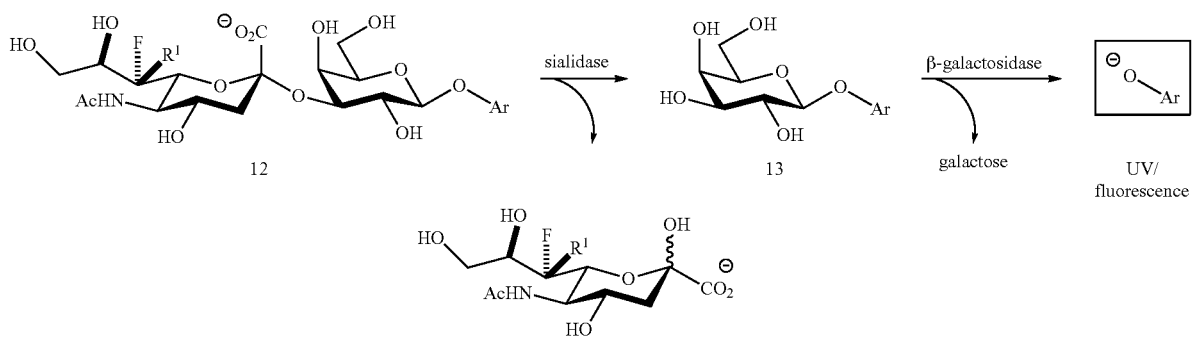

SCHEME 4-Overview of coupled kinetic assay

This kinetic assay requires a suitably fluorinated sialyl-galactoside substrate. However, rather than pursue a chemical glycosylation route to this substrate, which would require a multi-step and likely low-yielding synthesis[48], an enzymatic approach was taken instead. This required an α-2,3-sialyltransferase that was able to transfer the 7-fluoro sialic acid donor sugar derivatives to a suitable β-aryl-galactoside. If so, the desired sialidase substrates could be synthesised in one step. Additional advantages of this approach were that the effect of 7-fluorination on sialyl-transferase activity could be estimated en-route, and that the approach could be compatible with protein glycosylation conditions.

Example 3—Scheme 5

Sialyltransferases require a CMP-sialic acid as the donor substrate, and these can be readily obtained by enzymatic synthesis from the free sialic acid sugar using a CMP-sialic acid synthetase and CTP in the presence of an inorganic pyrophosphatase to drive the reaction to completion[49-51]. This approach has been demonstrated for the synthesis of several analogues, including CMP-7-deoxy-7-fluoro sialic acid[38]. Using standard conditions[52], both the CMP-7-deoxy-7-fluoro-sialic acid and CMP-7-deoxy-7,7-difluoro-sialic acids were synthesised using this approach and obtained in good yields of 86 and 62% after purification by ion-exchange and size exclusion chromatography.

Scheme 5-Synthesis of CMP-donors ii) cytidine triphosphate (1.05 eq.), CMP sialic acid synthetase (1 U/μmol), inorganic pyrophosphatase (1 U/mmol), 86% for 14 and 62% for 15;

R = H, 9
R = F, 11

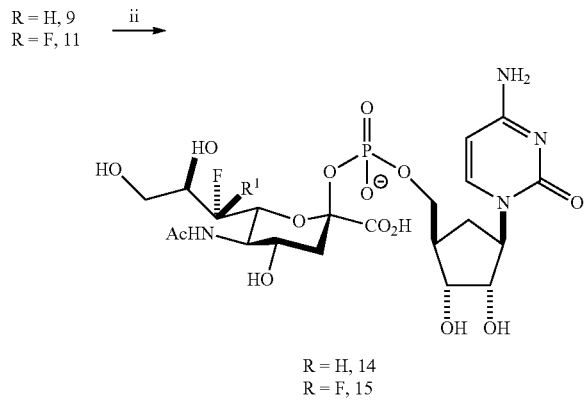

R = H, 14
R = F, 15

Example 4—Rate of Hydrolysis

The presence of a fluorine (or Br or Cl) at the 7-position should affect the transition state for hydrolysis or sialyl-transfer in two principal ways. The first is the inductive effect arising from the presence of a more electronegative element close to the centre of positive charge accumulating at the transition state. The second is the loss of a potential hydrogen-bond donor that occurs upon swapping the 7-hydroxyl for a halogen atom. Similar effects could be expected for ketone substitution; in addition, hydration of the ketone to the gem diol could lead to steric repulsion. These effects may deleteriously affect the interaction of the enzyme with the substrate at the transition state. This effect has been demonstrated on a similar system by observing the rates of spontaneous hydrolysis of a series of the analogous 6-deoxy-6-fluoro pyranosides. In the case where a dinitrophenol was used as the leaving group, the rates of hydrolysis was reduced by a factor of 0.35 by substitution with a fluorine at the 6-position[53], and similarly a reduction in hydrolysis rate of 0.27 was observed for the corresponding glucose-1-phosphates[54]. It might be expected that a similar decrease in spontaneous hydrolysis rate would be observed for CMP-7-deoxy-7-fluoro-NeuNAc 14. In an attempt to assess the contributions of each of these two effects on the rates of the sialidase or sialyltransferase reactions, the rates of spontaneous hydrolysis of each of the substrates were probed first. These results should provide some measure of the contribution of the inductive effect of the fluorine atom(s) to transition state destabilization in the absence of any specific hydrogen bonding effects.

TABLE 2A-2B - Relative rate constants for hydrolysis of sialosides.

| Compound | Rate constant for Hydrolysis | Rate Constant for sialidase (TRSA) | Rate Constant for sialidase (NanI) | Rate Constant for hydrolase (infl) |
|---|---|---|---|---|
| No-F | 1.45 | 254 | 133 | 1.8 |
| 7-F | 0.29 | 1 | 1 | 1 |

TABLE 2B

Rate constants for spontaneous hydrolysis of CMP-7-deoxy-7-fluoro modified sialic acids.

| Donor | # | Hydrolysis rate constant (h$^{-1}$) | k$_{rel}$ |
|---|---|---|---|
| CMP-NeuNAc | 16 | 0.94 (±0.01) | 1 |
| CMP-7-F-NeuNAc | 14 | 0.313 (±0.002) | 0.33 |
| CMP-7,7-diF-NeuNAc | 15 | 0.0084 (±0.0008) | 0.01 |

Figure 1B:
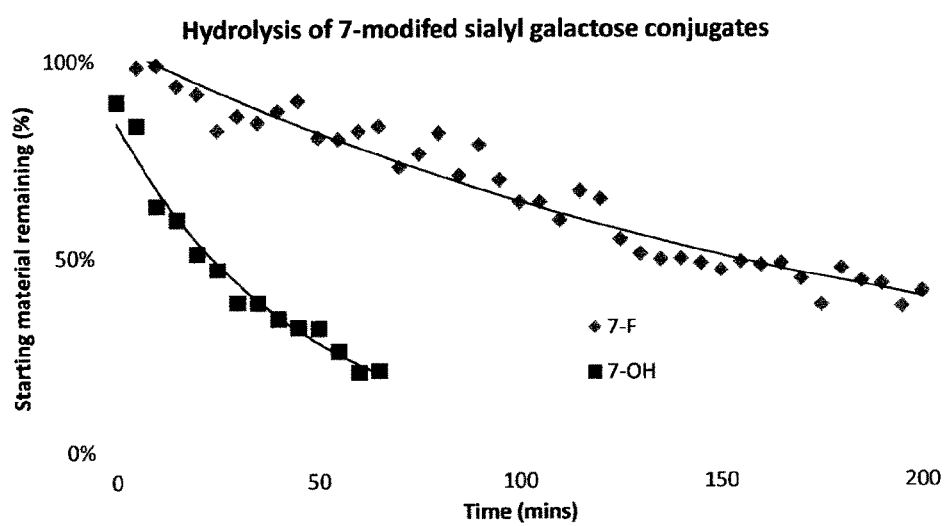
FIG. 1B shows a time course for hydrolysis of 7-modified sialyl-galactose conjugates at pH 7.2 and 60° C.

The rates of spontaneous hydrolysis of each of the 7-modified CMP-donors were measured at 600° C., in a high salt pH 7.2 buffer, by observing the changes in intensities of diagnostic protons over time, using $^1$H-NMR spectroscopy (see materials and methods). The decrease in intensity of each of these protons was monitored and fitted to a single exponential decay. The results (TABLES 2A and 2B) show that the substitution of a single fluorine atom at the 7-position causes around a three-fold decrease in hydrolysis rate constant relative to the parent, while introduction of 2 fluorine atoms resulted in a one hundred fold decrease. The presence of two fluorine atoms at the 7-position dramatically destabilises the transition state for spontaneous hydrolysis, making this CMP-NeuNAc derivative highly stable. As shown in FIG. 1A and FIG. 1B, the time course of hydrolysis of CMP 7-modified sialic acids and 7-modified sialyl-galactose conjugates, respectively were greatly influenced by the number of fluorine atoms.

Example 5—Sialyltransferase Substrates

Figure 2:
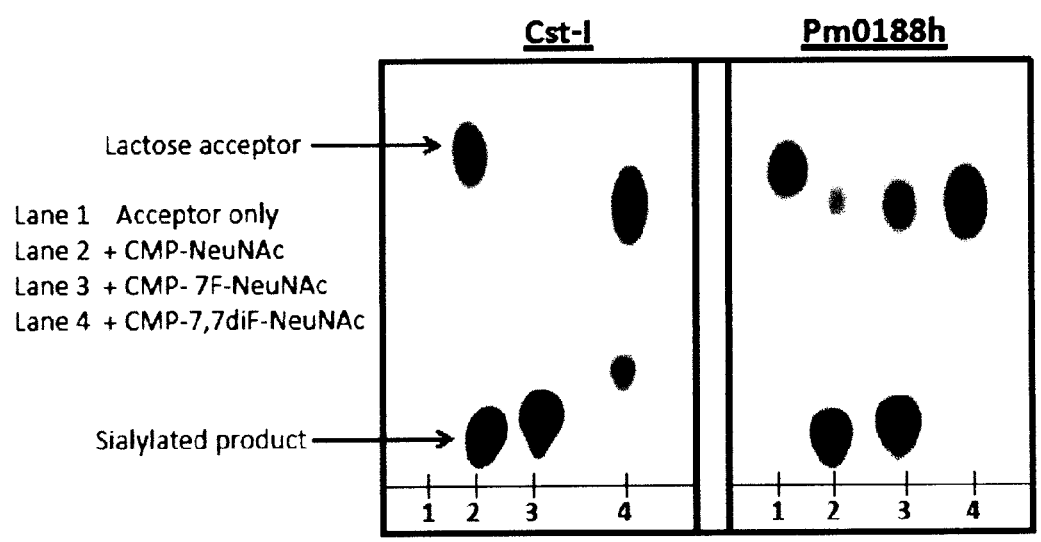
FIG. 2 shows a TLC analysis of sialyltransfer reaction of modified 7-fluoro sialic derivatives to Bodipy-lactose, catalyzed by Cst-I and Pmo188h.
Figure 3A:
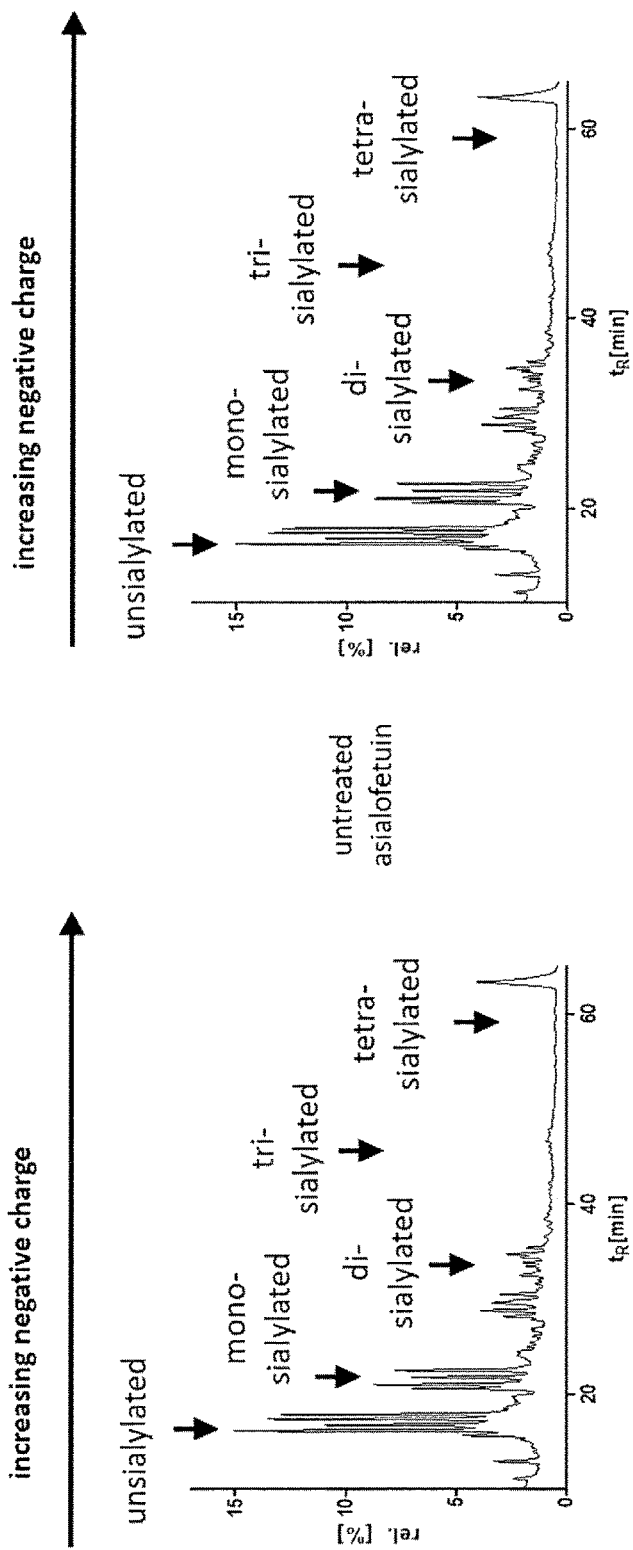
Figures 3B, 3C:
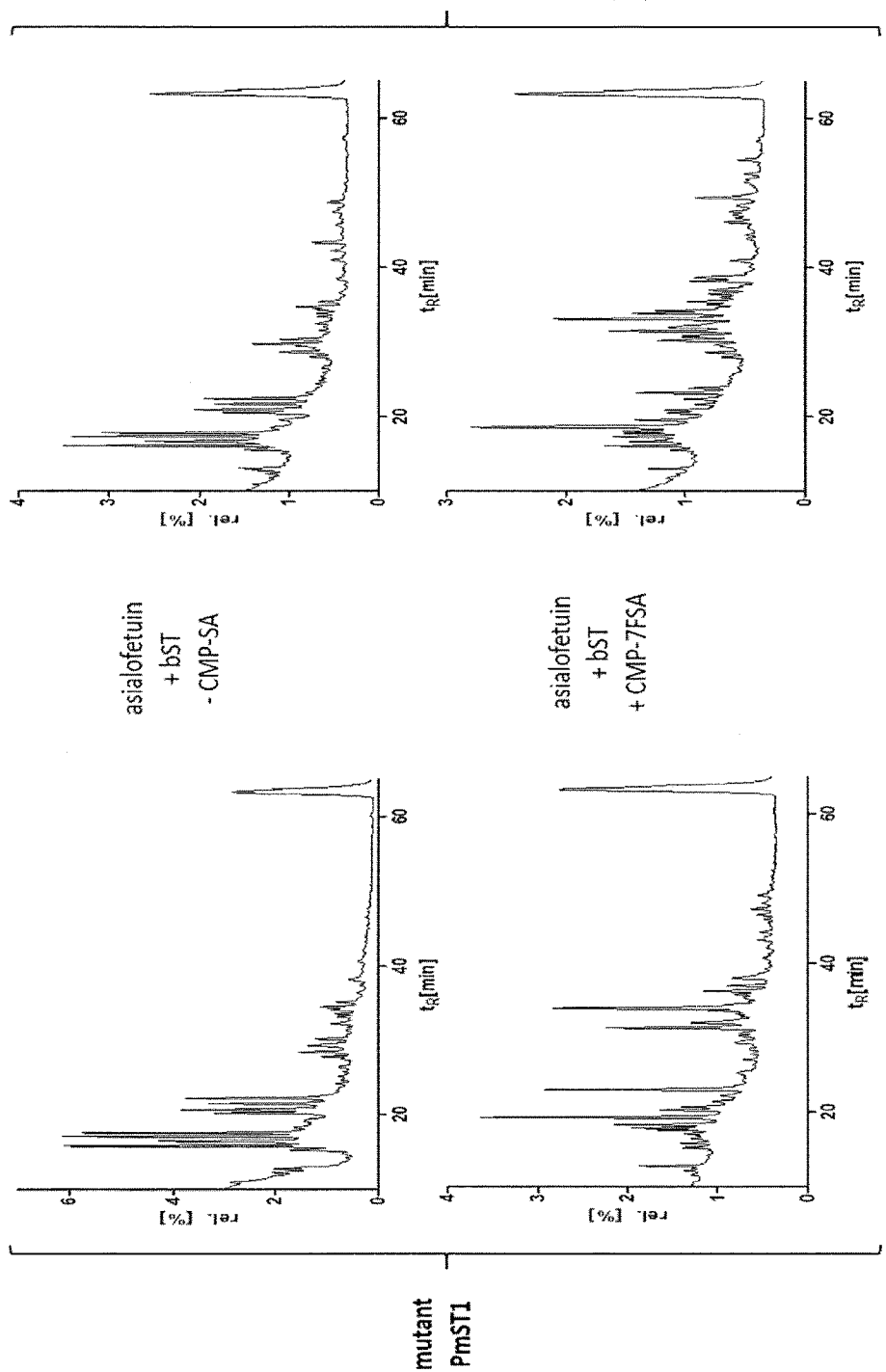
Figure 4:
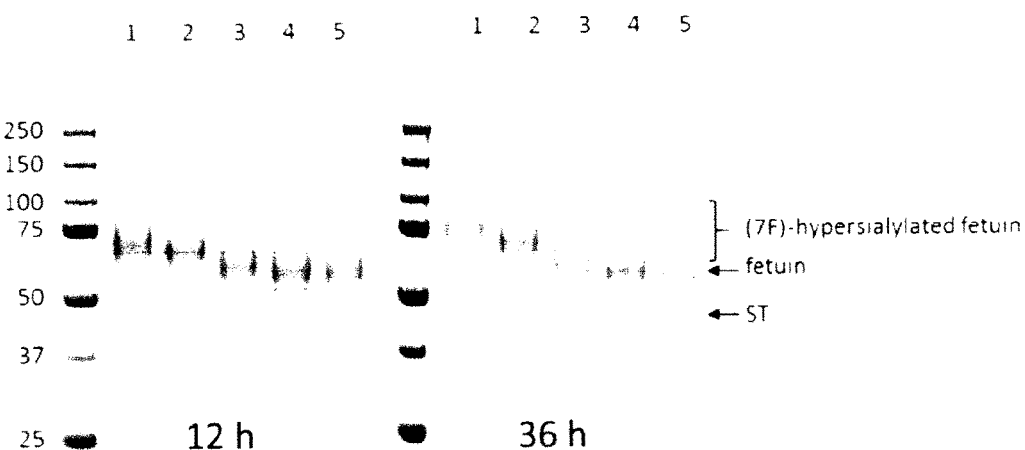
FIG. 4 shows mobility shift assays of (7F)-sialylation of fetuin by a mammalian sialyltransferase revealing coupling of 7FSA and SA.

Each of the 7-fluorinated CMP sialic acid sugar donors was tested as a substrate for each of two available sialyltransferases, Cst-I[31] from *C. jejuni* and a sialyltransferase from *Pasteurella* (Pmo188h)[55] in order to determine the effect of 7-fluorination on sialyltransferase activity. In each case an initial TLC assay was performed in which the sialyltransferase was incubated in the presence of a fluorescent BODIPY-lactose acceptor with two equivalents of the modified donor (FIG. 2). In the Cst-I catalyzed reactions, shown on the left, complete transfer of the natural donor 16 (lane 2) and the mono-fluoro donor 14 (lane 3) occurred after a ten minute incubation. Under these same conditions transfer of the difluoro donor 15 (lane 4) proceeded to around 20% completion, showing that this enzyme will transfer all of the modified donors to a lactose acceptor, albeit at different rates. Pmo188h was incubated with each of the 7-modified donors and the fluorescent lactose acceptor at pH 8.5, the optimum pH reported for α-2,3-sialyltransferase activity. Substantial differences in transfer rate are evident: after 5 minutes transfer of both the parent substrate 16 (lane 2) and mono-fluoro donor 14 (lane 3) are mostly complete, while only around 2% conversion of the difluoro donor 15 has occurred (lane 4). The latter progressed to 25% conversion after 18 hours (data not shown).

TABLE 3

Kinetic data for transfer from CMP-sialic derivatives
14, 15 and 16 to lactose by Cst-I and Pm0188h.

| | | # | $K_m$ (mM) | $k_{cat}$ (s$^{-1}$) | $k_{cat}/K_m$ (s$^{-1}$ mM$^{-1}$) | $k_{cat}$ (rel) |
|---|---|---|---|---|---|---|
| Cst-I | CMP-7OH | 16 | 0.87 (±0.06) | 4.2 (±0.2) | 5.6 (±0.4) | 1 |
| | CMP-7F | 14 | 0.55 (±0.06) | 3.2 (±0.2) | 5.8 (±0.7) | 0.77 |
| | CMP-7,7-diF | 15 | 0.42 (±0.04) | 1.1 (±0.1) | 2.5 (±0.2) | 0.25 |
| Pm0188h | CMP-7OH | 16 | 0.089 (±0.003) | 182 (±2) | 2045 (±80) | 1 |
| | CMP-7F | 14 | 0.052 (±0.003) | 99 (±1) | 1901 (±110) | 0.54 |
| | CMP-7,7-diF | 15 | 0.077 (±0.006) | 10.0 (±0.3) | 130 (±20) | 0.06 |

Having shown that both Cst-I and Pmo188h can catalyze the transfer of 7-modified sialic acids to lactose kinetic studies were carried out using a coupled assay to monitor CMP release, yielding the values shown in TABLE 3[56]. The broadly similar Km values for all three substrates revealed that there is no loss of binding in the ground state (Michaelis complex) as a consequence of fluorine substitution. Indeed, if anything binding is slightly improved. Further, while a decrease in the kcat values was observed, the effect is surprisingly small, with even the difluoro donor 16 being transferred at a rate that is 25% that of the natural donor.

The crystal structure of Cst-I[31], solved in the presence of CMP-3-fluoro sialic acid shows that the donor sugar binding site is not solvent accessible, and that only one distant contact (Asn66) is made between the 7-hydroxyl of the donor sugar and the enzyme. This may in part explain the tolerance of the enzyme to modifications at the 7-position since no significant hydrogen-bonding interactions are lost upon replacement of OH by F. This modest rate reduction relative to the 100-fold decrease in spontaneous hydrolysis rates upon difluorination may suggest that the transition state for the enzymatic reaction has much less oxocarbenium ion character than that of the spontaneous reaction since inductive effects would seem to be less important.

Detailed kinetic analysis for the sialyltransferase from Pasteurella (Pmo188h) was also performed[55]. This enzyme has been shown to be one of the most efficient catalysts for sialyltransfer, with kcat/Km values for transfer of CMP-NeuNAc that have been reported at over 300-fold higher than those of Cst-I. The kinetic analyses show that, as with Cst-I, Km values for each substrate were little affected by fluorine substitution. Likewise, substitution of a single fluorine only resulted in a 2-fold decrease in kcat. However, in contrast to the results from Cst-I, the kcat values were drastically decreased by further fluorine substitution, with the difluoro donor 15 being transferred ~20-fold slower than the natural donor. The crystal structure of this enzyme has been solved[33] and shows that most of the glycerol side chain of the donor sugar is solvent exposed, with the 7-hydroxyl making the only contact (Trp270). Based upon the monofluorosugar data, any interaction at that position cannot be very important. The large rate reduction may therefore indicate that the transition state for the GT80 Pasteurella sialyltransferase has much more oxocarbenium ion character than that for the GT42 Campylobacter enzyme.

Example 6—Scheme 6

SCHEME 6-Synthesis of substrate for sialidase kinetic analysis: oNP = ortho-nitrophenol; MU = 4-methylumbelliferyl

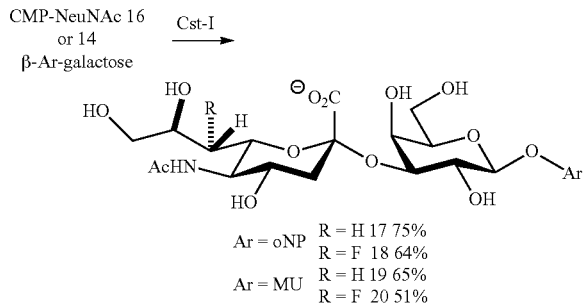

The synthesis of the desired sialidase substrates was accomplished using Cst-I, since TLC assays demonstrated that transfer using Cst-I could be pushed to completion, whereas reactions with the Pasteurella enzyme never did so, even in the presence of two equivalents of donor. This could be due to higher rates of enzyme-catalyzed hydrolysis of the donor that have been reported for this enzyme[57]. Two commercially available aryl β-galactosides, ortho-nitrophenyl (oNP) and 4-methylumbelliferyl (MU), were used as acceptor substrates for Cst-I, while the two 7-modified CMP sialic acid derivatives, along with CMP sialic acid itself, were used as donor substrates. The enzymatic coupling worked well for the natural 16 and mono-fluoro donor 14, but no transfer products were observed when the difluoro donor 15 was used. Nor were any products obtained when the more active Pasteurella enzyme was used. The discrepancy between this negative result and the positive results obtained in the other transferase assays could be attributed to the use of a lactose acceptor in the successful assays, whereas a monosaccharide acceptor is being used here. The combination of the non-natural 7,7-difluorinated donor and the loss of numerous hydrogen-bonding interactions from using a monosaccharide acceptor means that neither enzyme can catalyse the formation of a 7,7-difluoro-sialyl-galactose conjugate.

In order to determine the effect of fluorination at the 7-position on the intrinsic stability of the a-sialoside bond rate constants for the spontaneous hydrolysis of the methylumbelliferyl-containing sialyl-galactose conjugates 19 and 20 were measured using 1H-NMR spectroscopy (see materials and methods). The degradation was measured using a high salt, dilute acid solution of each substrate and by monitoring the change in intensities of diagnostic protons.

Since there are now two potential sugar linkages to be broken the position of hydrolysis was addressed by monitoring the changes in intensity of the anomeric proton of the galactose (H1') and the H3-equatorial proton of the sialic acid (H3"eq). These protons are diagnostic since their chemical shifts are exquisitely sensitive to changes in the anomeric configuration[58,59], and will show a measureable change in chemical shift during hydrolysis. These products were identified as the free sialic acid and the β-aryl-galactoside, by the appearance of a second proton with a very small upfield chemical shift of H1' and at a rate concurrent with the disappearance of H1' of the substrate. A large change in chemical shift of this proton would indicate hydrolysis of the β-O-aryl bond, indicating that the aryl-galactoside bond remains intact. It was also observed that the intensity of the H3" eq proton decreased without concurrent appearance of any other α-configured H3" eq protons[60], again indicating that the sialyl-galactose bond is being broken, rather than the aryl-galactose bond. This confirmed that the correct bond-breaking event is being observed and allowed the effect of 7-fluorination on the stability of the α-configured sialoside bonds to be addressed. This was achieved by monitoring the intensities of these protons over time and resulted in a spontaneous hydrolysis rate constant of 1.45 (±0.8) h-1 being measured for the 7-hydroxy-sialyl galactose 19 and 0.29 (±0.01) h-1 for the 7-fluoro sialyl galactose 20. These data suggest that substituting a fluorine at the 7-position imparts a five-fold increase in intrinsic stability of the a-sialoside bond. This is a slightly greater increase in stability, or destabilization of hydrolysis transition state, than that obtained for hydrolysis of the CMP-donors (three-fold), which have a β-configuration. However, since different leaving groups are used in each case a direct comparison is not meaningful.

Example 7—Kinetic Analysis of the Effect of 7-Fluorination on the Sialidase Activity A detailed kinetic analysis of the effect of 7-fluorination on sialidase activity was subsequently performed using sialidases from two different glycoside hydrolase families (GH33 and GH34)[37] using both a continuous-UV and a stopped-fluorescence assay. Two sialidases from family GH33, which contains all of the known eukaryotic sialidases, were tested, one from *T. rangeli* (TrSA)[61] and the second from *C. perfringens* (NanI)[62] using the coupled assay outlined in SCHEME 4. Saturation was not achieved in either case when using the 7-fluoro sialoside 18 substrate, even at high (>10 mM) substrate concentrations (TABLE 5).

As a result, only kcat/Km values could be obtained for comparison, and these reflect the rate constant of the first irreversible step in the enzymatic mechanism. The influenza neuraminidase N9 from the GH34 family was also tested with these substrates[63-66]. This family of hydrolases contains only viral sialidases and the active sites of enzymes therein are sufficiently different from those of GH33 enzymes to allow the development of selective inhibitors such as zanamivir and oseltamivir.

TABLE 4

Kinetic analysis of the effect of 7-fluorination on the sialidase activity of two family GH33 enzymes and one family GH34 hydrolase.

| Enzyme | Substrate | # | $K_m$ (mM) | $k_{cat}$ (min$^{-1}$) | $k_{cat}/K_m$ (min$^{-1}$mM$^{-1}$) | (rel) |
|---|---|---|---|---|---|---|
| *T. rangeli* | 7OH | 17 | 2.4 (±0.2) | 83 (±4) | 34 (±4) | 254 |
| (GH33) | 7F | 18 | ND | ND | 0.13 (±0.01) | 1 |
| *C. perfringens* | 7OH | 17 | 0.80 (±0.04) | 78 (±2) | 97 (±7) | 133 |
| (GH33) | 7F | 18 | ND | ND | 0.73 (±0.03) | 1 |

| | | | | $V_m$ (μM min$^{-1}$) | $V_m/K_m$ (min$^{-1}$ × 10$^{-3}$) | |
|---|---|---|---|---|---|---|
| *H. influenza* | 7OH | 17 | 0.83 (±0.06) | 17.5 (±0.5) | 21.2 (±2.0) | 1.8 |
| N9 (GH34) | 7F | 18 | 0.39 (±0.04) | 4.6 (±0.2) | 11.8 (±1.6) | 1 |

For both of the GH33 sialidases the kcat/Km values obtained for the 7-fluorinated sialoside substrate were less than 1% of that of the unmodified substrate. Clearly this reduction is much greater than that expected on due to inductive effects alone, on the basis of the spontaneous hydrolysis data, thus presumably also reflects loss of important non-covalent interactions at the active site. The X-ray crystal structures of both of these enzymes have been solved, both ligand-free and inhibitor-bound. In the case of the *Trypanosomal* sialidase OH7 is found to be part of a water-mediated hydrogen bonding network between the substrate and the enzyme, which includes interactions with Asn-60, the acid/base catalyst and also the C5-N-acetyl oxygen[24,28]. For the *Clostridium* sialidase OH7 is also involved in a tight water-mediated hydrogen bond network, this time to Asp-291, also the acid/base catalyst[30]. A significant restructuring of this hydrogen-bond network occurs upon ligand binding, along with a large displacement of Asn-60 or Asp-291, respectively, upon binding of substrate. Loss of the hydrogen bond to OH7 would therefore be expected to result in significant deleterious effects on the enzyme-catalyzed hydrolysis reaction. The consequence of this is that 7-deoxy-7-fluorosialosides are only slowly hydrolysed by GH33 sialidases. Since all mammalian sialidases belong to this family 7-fluorsialoside-containing glycoconjugates should be relatively stable in plasma.

For the family GH34 hydrolase only a two-fold preference for the natural substrate over the 7-fluoro analogue was observed, as reflected in the Vm/Km values. This is markedly different from the 100-fold rate differences observed for the family GH33 enzymes. Interestingly the difference in Vm values between the parent and 7-fluoro is almost exactly the same as for the spontaneous hydrolysis reactions (0.25 vs 0.20 respectively). Furthermore, the modified substrate was actually bound two-fold tighter than the parent. The structure of the group 2 influenza neuraminidases, of which N9 is a member, solved in the presence of an inhibitor[67] reveals only a very distant (3.8 Å) contact between the enzyme (Asp152) and the 7-position. These enzymes interact strongly with both OH8 and OH9, but only very weakly with OH7. This may explain the tolerance of the enzyme towards modifications at the 7-position, since there are essentially no enzyme-substrate interactions around this position, and removing the hydrogen bond donor of the substrate has little effect. This is in stark contrast with the family GH33 enzyme whereby the enzyme-substrate contacts around the 7-hydroxyl are important for activity of the enzyme.

Sialic acids bearing multiple fluorine atoms at the 7-position have been successfully synthesized using an epimerase-aldolase two-enzyme system to convert 4-fluorinated GlcNAc derivatives directly to their corresponding sialic acids. They have been converted to their CMP conjugates and these were tested as substrates for two sialyltransferases from Campylobacter and Pasteurella. Of these two enzymes Cst-I was found to be the superior catalyst for transfer of the modified sugars, and was used to synthesise 7-modified sialyl-galactosides bearing chromogenic groups at the galactose anomeric centre.

The effect of substituting a more electronegative fluorine atom at the 7-position, close to the build of positive charge on the ring oxygen during spontaneous hydrolysis, on rate constants for sialoside hydrolysis was investigated using $^1$H-NMR. It was found that a single fluorine atom at C-7 reduced hydrolytic rate constants for the CMP and sialyl-galactose conjugates by three- and four-fold respectively, consistent with expectations based upon equivalent replacements (at the 6-position) in hexopyranosides[53,54]. Furthermore the insertion of a second fluorine at this position stabilized the CMP-conjugate by 100-fold over the natural substrate. This much larger effect is consistent with the fact that the second fluorine formally replaces a hydrogen rather than a hydroxyl[68]. Overall these results align with the work of Horenstein in which multiple kinetic isotope effect studies showed that non-enzymatic hydrolysis of CMP NeuNAc occurs via a very late oxocarbenium ion-like transition state, as might be expected for such a reaction at a tertiary (ketal) centre[69].

The sialyl-galactose conjugates were tested as substrates for sialidases of two different glycoside hydrolase families, GH33 and GH34, using a stopped-fluorescence coupled-assay and it was found that the neuraminidase N9 was tolerant to modifications at the 7-position, with a minimal impact on enzyme efficiency. However the enzymes tested from family GH33 were found to be intolerant to 7-deoxyfluorination, with $k_{cat}/K_m$ values less than 0.5% that of substrates bearing a 7-hydroxyl group. This was attributed to the importance of hydrogen bond contacts made through OH7 to the enzyme during catalysis, contacts that are not present in the GH34 enzyme. For this N9 enzyme most of the rate loss can be attributed to the inductive effect arising from a fluorine atom close to the ring oxygen. These results have important implications in the design and synthesis of metabolically stable therapeutic glycoproteins. All known mammalian sialidases are members of family GH33, thus can be expected to cleave these 7-fluorosialosides only very slowly. However, since the sialyltransferases used here are quite capable of synthesising the 7-fluorosialosides they may be used to transfer 7-deoxyfluorinated sialic acids to glycoproteins bearing galactose-terminated glycans. These glycoproteins, terminated in the modified sialosides, would thus be resistant to any sialidase in blood plasma, thereby decreasing the clearance rate and increasing the efficacy of any glycotherapeutic.

Example 8—Protein α2,3-(7F)-Sialylation by Mutant Bacterial Sialyltranferases (ST)

Bacterial sialyltransferases are valuable tools for glyco-engineering because they can be recombinantly produced in large amounts by exploiting well-established bacterial/yeast expression systems. Although they readily accept a wide range of oligosaccharides as acceptor substrate, their major drawback is generally their poor activity on glycoproteins. Provided herein is an example with two bacterial enzymes, a mutant PmST1 and Cst-I, that are capable of modifying a model protein, asialofetuin, with SA and 7FSA. Fetuin was chosen as the model protein, since it has been well studied for decades, and it is heavily glycosylated with a mixture of O- and N-glycans (4 and 3, respectively), which branches are capped to >95% with α2,3- and α2,6 linked sialic acid.

Although large mobility shifts were not observed on reducing SDS-PAGE gels in either case (i.e. SA or 7FSA), and reasonable shifts were detected by using HPAEC-PAD (FIG. 3). The chromatogram of in vitro sialylated asialofetuin strongly resembles that of untreated fetuin, as would be expected if the protein has been re-sialylated whereas. Modification by 7F-sialylation is less efficient, but is clearly occurring. Since the transfer of 7FSA is slower than that of SA, even onto small acceptor substrates, the pattern is most likely a consequence of lower reaction rates and/or adverse product hydrolysis rather than incompatibility. In addition, the broader variety of peaks and slight peak group shift to the right reflects the insertion of a strong electron-withdrawing group, which allows for better deprotonation of adjacent hydroxyl groups under the high pH conditions of the HPAEC-PAD system employed in this analysis.

The overall results are promising and show that these proteins can be 7-fluorosialylated using the sialyltransferases available. This might be improved by use of higher concentrations of the sialyltransferases, or by improving these enzymes through directed evolution. In any case, reaction conditions for less complex glycosylated proteins bearing more homogenous glycans may be optimized towards satisfying yields.

Example 9—Protein α2,8-Sialylation by a Recombinant Mammalian Sialyltransferase (ST) Variant The potential of mammalian enzymes to load 7FSA from the donor substrate CMP-7FSA onto a model protein (bovine fetuin) was tested. In this example, the experiments made use of a truncated oligosialyltransferase variant (CAZy classification GT 29 family) which is known to attach multiple SA α2,8-linked to α2,3-sialyl acceptors. The enzyme was recombinantly expressed in a baculovirus insect cell system and extensively purified with three sequential chromatography steps.

Time-course sialylation experiments show mobility shifts due to enzymatic hypersialylation of fetuin, which is heavily sialylated (FIG. 4). Incorporation of 7FSA gave a slight but clear shift. However, the shift was much more pronounced in the case of sialic acid, indicating a much higher total loading of sialic acid moieties onto the protein. Use of longer reaction times did not increase the amount of 7FSA transferred (data not shown). This suggests that the enzyme, a putative oligosialyltransferase, is not able to transfer more than one 7FSA per branch, but is able to do so in the case of SA (mass shift 15-20 kDa corresponding to around 50-60 SA units). This suggests that once the glycan structures have been "endcapped" with one 7FSA moiety any further transfer is prevented. Indeed, high-resolution X-ray structures of this particular sialyltransferase in complex with a competent acceptor substrate, namely 3'-sialyl-6-sulfo-LacNAc, reveal hydrogen bonding interactions between the 7-OH group of the acceptor sialyl unit and an arginine residue (data not shown). In the case of 7FSA this hydroxyl group is replaced by a fluorine atom, hence, an important hydrogen bonding partner is missing, which most likely results in improper acceptor orientation and binding. This feature is of particular interest for the production of terminal disialyl motifs as they are found increasingly on both, N- and O-glycan structures. In an addition control experiment, α1-antitrypsin, which is covered mainly by 2,6-linked sialic acids, and asialofetuin were treated similar but no sign of sialylation was observed. This is in good agreement with literature reports showing that this enzyme only modifies glycans that are already "primed" with at least one α2,3-linked sialic acid.

Furthermore, addition of dextran-40 as a molecular crowder[82] had a beneficial effect on the overall transfer, thereby, increasing the extent-rate of addition of 7FSA and SA. This molecular crowding effect will be particularly important in the large-scale modification of therapeutic proteins in order to reduce reaction times and material costs.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

REFERENCES

1. B. Leader, Q. J. Baca, D. E. Golan, Nature Reviews Drug Discovery 7:21 (2008).
2. S. R. Schmidt, Current Opinion in Drug Discovery & Development 12:284 (March, 2009).
3. C. N. Belcher, N. Vij, Current Molecular Medicine 10:82 (2010).
4. C. W. Shuptrine, R. Surana, L. M. Weiner, Seminars in Cancer Biology 22, 3 (February, 2012).
5. G. Walsh, Nature Biotechnology 28:917 (September, 2010).
6. I. B. Hirsch, New England Journal of Medicine 352:174 (2005).
7. Z. Kiss, S. Elliott, K. Jedynasty, V. Tesar, J. Szegedi, European Journal of Clinical Pharmacology 66:331 (2010).
8. V. K. Rustgi, Current Medical Research and Opinion 25:991 (2009).
9. M. Sauerborn, V. Brinks, W. Jiskoot, H. Schellekens, Trends in Pharmacological Sciences 31:53 (2010).
10. D. P. Gamblin, E. M. Scanlan, B. G. Davis, Chemical Reviews 109:131 (January, 2009).
11. L. K. Mahal, Anti-Cancer Agents in Medicinal Chemistry 8:37 (2008).
12. R. J. Sola, K. Griebenow, Journal of Pharmaceutical Sciences 98:1223 (2009).
13. J. Du et al., Glycobiology 19:1382 (Dec. 1, 2009, 2009).
14. A. G. Morell, Gregoria. G, Scheinbe. Ih, J. Hickman, G. Ashwell, Journal of Biological Chemistry 246:1461 (1971).
15. I. G. McFarlane, B. M. McFarlane, G. N. Major, P. Tolley, R. Williams, Clinical and Experimental Immunology 55:347 (1984).
16. W. E. Pricer, G. Ashwell, Journal of Biological Chemistry 246:4825 (1971).
17. B. Agoram et al., Journal of Pharmaceutical Sciences 98:2198 (2009).
18. A. Buschiazzo, P. M. Alzari, Current Opinion in Chemical Biology 12:565 (October, 2008).
19. J. C. Wilson, M. J. Kiefel, D. I. Angus, M. von Itzstein, Organic Letters 1:443 (1999).
20. L. D. Powell, R. K. Jain, K. L. Matta, S. Sabesan, A. Varki, Journal of Biological Chemistry 270:7523 (Mar. 31, 1995, 1995).
21. R. R. Kale et al., Journal of the American Chemical Society 130:8169 (2008).
22. J. R. Rich, D. R. Bundle, Organic Letters 6:897 (2004).
23. J. R. Rich, W. W. Wakarchuk, D. R. Bundle, Chemistry—a European Journal 12:845 (2006).
24. M. F. Amaya, A. Buschiazzo, T. Nguyen, P. M. Alzari, Journal of Molecular Biology 325:773 (2003).
25. A. Buschiazzo, M. F. Amaya, M. L. Cremona, A. C. Frasch, P. M. Alzari, Molecular Cell 10:757 (2002).
26. A. Liakatos, M. J. Kiefel, F. Fleming, B. Coulson, M. von Itzstein, Bioorganic & Medicinal Chemistry 14:739 (2006).
27. J. I. Sakamoto et al., Bioorganic & Medicinal Chemistry 17:5451 (2009).
28. A. G. Watts, P. Oppezzo, S. G. Withers, P. M. Alzari, A. Buschiazzo, Journal of Biological Chemistry 281:4149 (February, 2006).
29. A. G. Watts, S. G. Withers, Canadian Journal of Chemistry 82:1581 (2004).
30. S. L. Newstead et al., Journal of Biological Chemistry 283:9080 (April, 2008).
31. C. P. C. Chiu et al., Biochemistry 46:7196 (2007).
32. C. P. C. Chiu et al., Nature Structural & Molecular Biology 11:163 (February, 2004).
33. L. S. Ni et al., Biochemistry 46:6288 (May, 2007).
34. M. D. Burkart, S. P. Vincent, C. H. Wong, Chemical Communications, 1525 (August, 1999).
35. S. G. Withers, I. P. Street, P. Bird, D. H. Dolphin, Journal of the American Chemical Society 109:7530 (1987).
36. S. G. Withers, M. D. Percival, I. P. Street, Biochemistry 27:3078 (April, 1988).
37. B. L. Cantarel et al., Nucleic Acids Research 37: D233 (January, 2009).
38. S. Hartlieb et al., Carbohydrate Research 343:2075 (2008).
39. T. Honda et al., Bioorganic & Medicinal Chemistry Letters 12:1921 (2002).
40. I. Hemeon, A. J. Bennet, Synthesis-Stuttgart, 1899 (2007).

41. M. Sharma, R. J. Bernacki, B. Paul, W. Korytnyk, Carbohydrate Research 198:205 (1990).
42. R. Thomson, M. Vonitzstein, Carbohydrate Research 274:29 (1995).
43. S. Y. Hu et al., Applied Microbiology and Biotechnology 85:1383 (2010).
44. J. A. Harrison et al., Bioorganic & Medicinal Chemistry Letters 11, 141 (2001).
45. D. Indurugalla, J. N. Watson, A. J. Bennet, Organic & Biomolecular Chemistry 4:4453 (2006).
46. H. Z. Cao et al., Organic & Biomolecular Chemistry 7:5137 (2009).
47. K. Wallenfels, O. P. Malhotra, Advances in Carbohydrate Chemistry 16:239 (1961).
48. D. K. Ress, R. J. Linhardt, Current Organic Synthesis 1:31 (2004).
49. M. F. Karwaski et al. Protein Expression and Purification 25:237 (2002).
50. J. Nahalka, V. Patoprsty, Organic & Biomolecular Chemistry 7:1778 (2009).
51. R. M. Mizanur, N. L. Pohl, Applied Microbiology and Biotechnology 80:757 (2008).
52. T. J. Morley, S. G. Withers, Journal of the American Chemical Society 132:9430 (Jul. 14, 2010).
53. M. N. Namchuk, J. D. McCarter, A. Becalski, T. Andrews, S. G. Withers, Journal of the American Chemical Society 122:1270 (February, 2000).
54. S. G. Withers, D. J. Maclennan, I. P. Street, Carbohydrate Research 154, 127 (1986).
55. H. Yu et al., Journal of the American Chemical Society 127:17618 (2005).
56. S. Gosselin et al. Analytical Biochemistry 220:92 (1994).
57. G. Sugiarto et al., Acs Chemical Biology 7:1232 (July, 2012).
58. U. Dabrowski, H. Friebolin, R. Brossmer, M. Supp, Tetrahedron Letters 20:4637 (1979).
59. R. U. Lemieux, J. D. Stevens, Canadian Journal of Chemistry 43:2059 (1965).
60. Y. H. Kao, L. Lerner, T. G. Warner, Glycobiology 7:559 (June, 1997).
61. G. Reuter, R. Schauer, R. Prioli, M. E. A. Pereira, Glycoconjugate Journal 4, 339 (1987).
62. C. Traving, R. Schauer, P. Roggentin, Glycoconjugate Journal 11:141 (1994).
63. Y. Chander, N. Jindal, D. E. Stallknecht, S. Sreevatsan, S. M. Goyal, Journal of Virological Methods 165:116.
64. O. Aruksakunwong et al., Biophysical Journal 92:798 (February, 2007).
65. K. Veluraja, M. X. Suresh, T. H. T. Christlet, Z. A. Rafi, Journal of Biomolecular Structure & Dynamics 19:33 (August, 2001).
66. M. Vonitzstein et al., Nature 363:418 (June, 1993).
67. P. Bossart-Whitaker et al., Journal of Molecular Biology 232:1069 (1993).
68. R. Zhang et al., Journal of Organic Chemistry 73:3070 (April, 2008).
69. B. A. Horenstein, M. Bruner, Journal of the American Chemical Society 118:10371 (October, 1996).
70. Karwaski, M. F., Wakarchuk, W. W., and Gilbert, M., (2002) Protein Expression Purif. 25, 237-240.
71. Chiu, C. P. C., Lairson, L. L., Gilbert, M., Wakarchuk, W. W., Withers, S. G., and Strynadka, N. C. J., (2007) Biochemistry 46:7196-7204.
72. Yu, H., Chokhawala, H., Karpel, R., Yu, H., Wu, B. Y., Zhang, J. B., Zhang, Y. X., Jia, Q., and Chen, X., (2005) J. Am. Chem. Soc. 127:17618-17619.
73. Gosselin, S., Alhussaini, M., Streiff, M. B., Takabayashi, K., and Palcic, M. M., (1994) Anal. Biochem. 220:92-97.
74. Harrison, J. A., Kartha, K. P. R., Turnbull, W. B., Scheuerl, S. L., Naismith, J. H., Schenkman, S., and Field, R. A., (2001) Bioorg. Med. Chem. Lett. 11:141-144.
75. Cao, H. Z., Li, Y. H., Lau, K., Muthana, S., Yu, H., Cheng, J. S., Chokhawala, H. A., Sugiarto, G., Zhang, L., and Chen, X., (2009) Org. Biomol. Chem 7:5137-5145.
76. Sharma, M., Bernacki, R. J., Paul, B., and Korytnyk, W., (1990) Carbohydr. Res. 198: 205-221.
77. Hartlieb, S., Gunzel, A., Gerardy-Schahn, R., Munster-Kuhnel, A. K., Kirschning, A., and Drager, G., (2008) Carbohydr. Res. 43:2075-2082.
78. Indurugalla, D., Watson, J. N., and Bennet, A. J., (2006) Org. Biomol. Chem 4:4453-4459.
79. Leader, B., Baca, Q. J., and Golan D. E. (2008) Nature Reviews-Drug Discovery 7:11-39.
80. Kaspar, A. A., and Reichert, J. M. (2013) Drug Discovery Today 18 (17-18):807-817.
81. Kolarich D, Weber A, Turecek P L, Schwarz H P, Altmann F. Comprehensive glyco-proteomic analysis of human alphas-antitrypsin and its charge isoforms. Proteomics. 2006; 6(11):3369-80.
82. Chapanian R, Kwan D H, Constantinescu I, Shaikh F A, Rossi N A, Withers S G, Kizhakkedathu J N. Enhancement of biological reactions on cell surfaces via macromolecular crowding. Nat Commun. 2014; 5:4683.

What is claimed is:

1. A compound of Formula I or a pharmaceutically acceptable salt thereof:

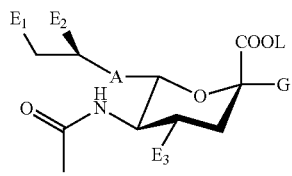

wherein

A is

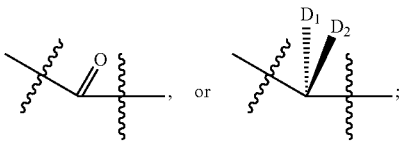

$D_1$ is selected from H, F, Cl and Br;
$D_2$ is selected from H, F, Cl and Br;
$E_1$ is selected from OH and an ester;
$E_2$ is selected from OH and an ester;
$E_3$ is selected from OH and an ester;
L is H, Me, Et, Pr, Bu, pentyl, hexyl, heptyl, octyl, nonyl, or decyl;
G is OH, CMP or a substituted phenol;
provided that both $D_1$ and $D_2$ are not both H; and provided that when L is H and G is OH, A is selected from

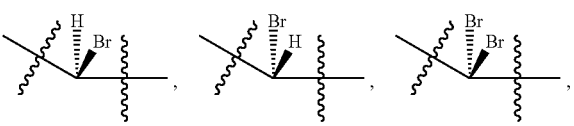

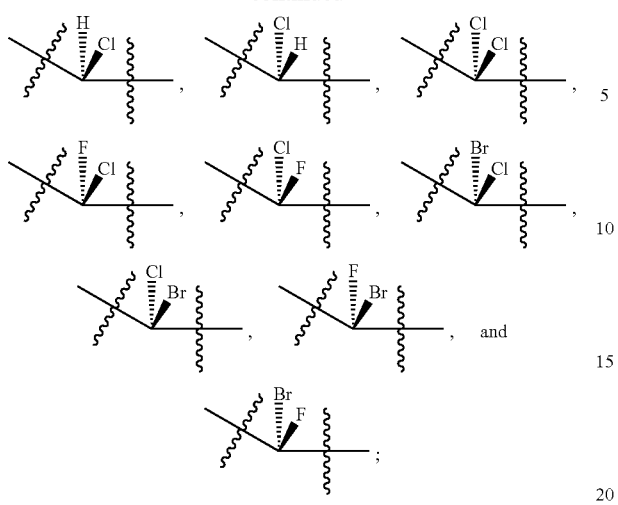

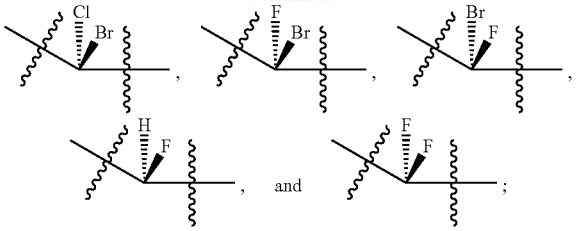

wherein the ester is independently selected from one or more of the following: a linear or branched acetate, a linear or branched propionate, a linear or branched butyrate, a linear or branched pentanoate, a linear or branched hexanoate, a linear or branched heptanoate, a linear or branched octanoate, a linear or branched nonanoate, and a linear or branched decanoate; and wherein the compound is further covalently bound to a protein or a glycolipid.

2. The compound of claim 1, wherein the glycoprotein is mucin-linked or is asparagine-linked.

3. A compound having the structure of Formula II or a pharmaceutically acceptable salt thereof:

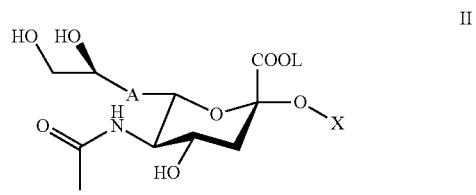

II and provided that when L is Me and G is OH, A is selected from

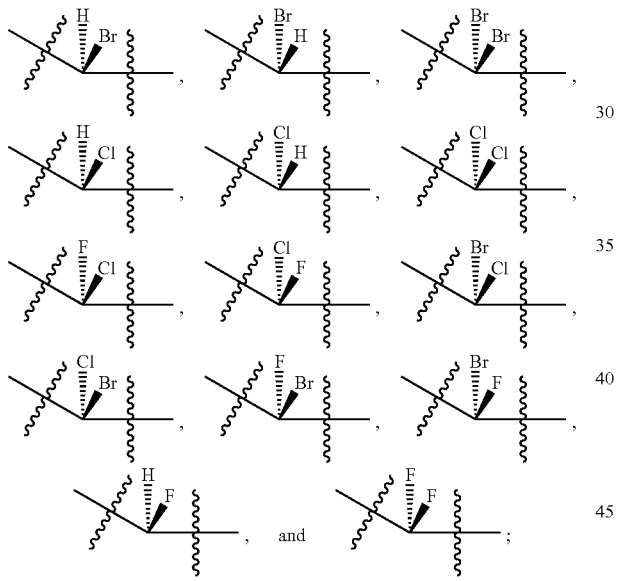

wherein
A is

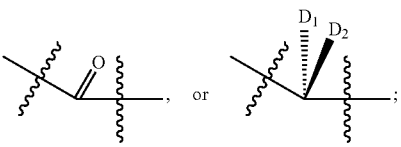

$D_1$ is selected from H, F, Cl and Br;
$D_2$ is selected from H, F, Cl and Br;
L is H, or $CH_3$;
X is a sialic acid, a modified sialic acid, or β-D-Galactose;
provided that both $D_1$ and $D_2$ are not both H,
wherein the compound is further covalently bound to a glycoprotein.

4. The compound of claim 3, wherein the glycoprotein is mucin-linked or is asparagine-linked.

5. A compound having the structure of Formula II or a pharmaceutically acceptable salt thereof:

and provided that when L is H and G is CMP, A is selected from

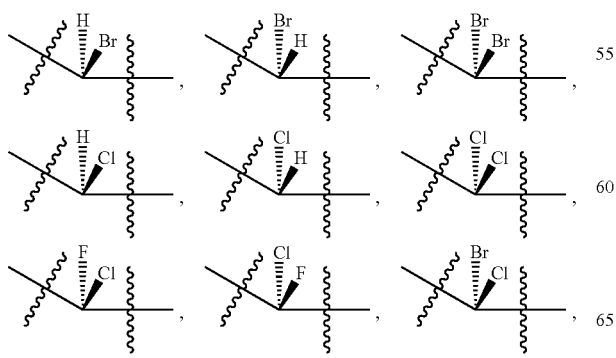

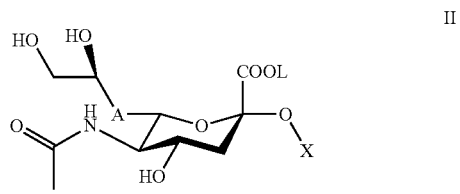

II wherein
A is
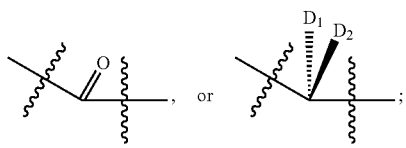
$D_1$ is selected from H, F, Cl and Br;
$D_2$ is selected from H, F, Cl and Br;
L is H, or $CH_3$;
X is a sialic acid, a modified sialic acid, or P-D-Galactose;
provided that both $D_1$ and $D_2$ are not both H,
wherein the compound is further covalently bound to a protein.
6. The compound of claim 5, wherein the glycoprotein is mucin-linked or is asparagine-linked.
* * * * *

UNITED STATES PATENT AND TRADEMARK OFFICE
CERTIFICATE OF CORRECTION

PATENT NO. : 10,023,601 B2
APPLICATION NO. : 15/119622
DATED : July 17, 2018
INVENTOR(S) : Stephen G. Withers et al.

It is certified that error appears in the above-identified patent and that said Letters Patent is hereby corrected as shown below:

In the Specification

Column 25,
Line 26, "to 600°C. for" should read -- to 60°C. for --.
Line 47, "at 600°C. for" should read -- at 60°C. for --.

Column 29,
Line 27, "acid)-(23)-β" should read -- acid)-(2→3)-β --.

Column 31,
Line 35, "pH 7-5 with" should read -- pH 7.5 with --.

Column 39,
Line 47, "a-sialoside bond." should read -- α-sialoside bond. --.

In the Claims

Column 49,
Line 15, "P-D-Galactose;" should read -- β-D-Galactose; --.

Signed and Sealed this
Thirtieth Day of April, 2019

Andrei Iancu
*Director of the United States Patent and Trademark Office*